US011793216B2

(12) United States Patent
Watson et al.

(10) Patent No.: US 11,793,216 B2
(45) **Date of Patent: *Oct. 24, 2023**

(54) ANIMAL FEED COMPOSITIONS AND METHODS OF USE

(71) Applicant: Syngenta Participations AG, Basel (CH)

(72) Inventors: Eileen Dorothea Watson, Greensboro, NC (US); David Witherspoon, Oak Island, NC (US); Tammiraj Kumar Iragavarapu, Minnetonka, MN (US)

(73) Assignee: Syngenta Participations AG, Basel (CH)

( * ) Notice: Subject to any disclaimer, the term of this patent is extended or adjusted under 35 U.S.C. 154(b) by 587 days.

This patent is subject to a terminal disclaimer.

(21) Appl. No.: 16/650,526

(22) PCT Filed: Oct. 10, 2018

(86) PCT No.: PCT/US2018/055169

§ 371 (c)(1),
(2) Date: Mar. 25, 2020

(87) PCT Pub. No.: WO2019/075028

PCT Pub. Date: Apr. 18, 2019

(65) Prior Publication Data

US 2020/0315212 A1 Oct. 8, 2020

Related U.S. Application Data

(60) Provisional application No. 62/571,378, filed on Oct. 12, 2017.

(51) Int. Cl.
*A23K 10/30* (2016.01)
*A23K 20/142* (2016.01)
(Continued)

(52) U.S. Cl.
CPC ........... *A23K 10/30* (2016.05); *A23K 20/142* (2016.05); *A23K 20/153* (2016.05); *A23K 50/10* (2016.05)

(58) Field of Classification Search
CPC .... A23K 10/30; A23K 20/142; A23K 20/153; A23K 50/10; A23K 20/189; Y02P 60/87;
(Continued)

(56) References Cited

U.S. PATENT DOCUMENTS 5,543,576 A 8/1996 van Ooijen et al.
5,714,474 A 2/1998 Van Ooijen et al.
(Continued)

FOREIGN PATENT DOCUMENTS

CN 106721009 A 5/2017
EP 0449376 B1 5/2001
(Continued)

OTHER PUBLICATIONS

"Application for import and use of genetically modified Event 3272 maize under Regulation (EC) No. 1829/2003", obtained from https://euginius.eu/euginius/api/literature/pdf/2170524150539240096, published 2013, 28 pages (2013).
(Continued)

*Primary Examiner* — Savitha M Rao
*Assistant Examiner* — Andrew P Lee
(74) *Attorney, Agent, or Firm* — Karen A. Magri

(57) ABSTRACT

The invention provides an animal feed composition comprising microbial α-amylase, for example, an animal feed composition comprising transgenic plant material comprising a microbial α-amylase (e.g., a thermostable microbial α-amylase). The invention further provides methods of increasing animal performance and/or the efficiency of feed
(Continued)

utilization by an animal (e.g., for milk or meat production), comprising feeding to the animal an animal feed composition of the present invention.

19 Claims, 3 Drawing Sheets

Specification includes a Sequence Listing.

(51) Int. Cl.
*A23K 20/153* (2016.01)
*A23K 50/10* (2016.01)

(58) Field of Classification Search
CPC . C12N 9/2408; C12N 9/2417; C12N 15/8245
See application file for complete search history.

(56) References Cited

U.S. PATENT DOCUMENTS

| | | | |
|---|---|---|---|
| 6,623,750 B1 | 9/2003 | Cobb et al. | |
| 7,033,627 B2 | 4/2006 | Van Ooyen et al. | |
| 7,102,057 B2 | 9/2006 | Lanahan et al. | |
| 7,407,677 B2 | 8/2008 | Callen et al. | |
| 7,557,262 B2 | 7/2009 | Lanahan et al. | |
| 7,635,799 B2 | 12/2009 | Johnson et al. | |
| 7,727,726 B2 | 6/2010 | Cates et al. | |
| 7,781,201 B2 | 8/2010 | Callen et al. | |
| 7,785,855 B2 | 8/2010 | Callen et al. | |
| 7,816,108 B2 | 10/2010 | Callen et al. | |
| 7,855,322 B2 | 12/2010 | Lanahan et al. | |
| 7,914,993 B2 | 3/2011 | Batie et al. | |
| 7,915,020 B2 | 3/2011 | Cates et al. | |
| 7,919,681 B2 | 4/2011 | Lanahan et al. | |
| 8,003,863 B1 | 8/2011 | Goodwin | |
| 8,093,453 B2 | 1/2012 | Johnson et al. | |
| 9,018,447 B2 | 4/2015 | Lanahan et al. | |
| 9,125,357 B2 | 9/2015 | Dallmier et al. | |
| 9,816,119 B2 | 11/2017 | Aux | |
| 10,100,324 B2 | 10/2018 | Ral et al. | |
| 10,196,669 B2 | 2/2019 | Costello et al. | |
| 2003/0135885 A1 | 7/2003 | Lanahan et al. | |
| 2004/0202697 A1 | 10/2004 | Beauchemin et al. | |
| 2006/0230473 A1 | 10/2006 | Johnson et al. | |
| 2007/0243236 A1 | 10/2007 | Cerda et al. | |
| 2009/0032471 A1 | 2/2009 | Borg | |
| 2009/0324571 A1 | 12/2009 | Steinberg et al. | |
| 2011/0117067 A1* | 5/2011 | Esteghlalian | E21B 43/26 435/254.11 |
| 2014/0234279 A1 | 8/2014 | Millan | |
| 2016/0108383 A1 | 4/2016 | Hitchman et al. | |
| 2016/0324190 A1 | 11/2016 | DeLord et al. | |
| 2017/0101663 A1 | 4/2017 | Moser et al. | |
| 2018/0030491 A1 | 2/2018 | Aux | |

FOREIGN PATENT DOCUMENTS

| | | |
|---|---|---|
| RU | 2 073 715 C1 | 2/1997 |
| RU | 2 533 001 C2 | 11/2014 |
| UA | 10246 | 12/1996 |
| WO | 2003000905 A2 | 1/2003 |
| WO | 2003/018766 A3 | 3/2003 |
| WO | 03/059087 A1 | 7/2003 |
| WO | 2005096804 A2 | 10/2005 |
| WO | 2006098952 A2 | 9/2006 |
| WO | 2009/140504 A1 | 11/2009 |
| WO | 2010088447 A1 | 8/2010 |
| WO | 2010091221 A1 | 8/2010 |
| WO | 2012004759 A2 | 1/2012 |
| WO | 2016/164732 A2 | 10/2016 |
| WO | 2018/204245 A1 | 11/2018 |

OTHER PUBLICATIONS

"Novel Food Information", obtained from https://www.canada.ca/en/health-canada/services/food-nutrition/genetically-modified-foods-other-novel-foods/approved-products/alpha-amylase-corn-event-3272.html; published 2008 7 pages (2008).

"Scientific Opinion", EFSA J. 11:3252, 2013, 27 pages (2013).

Kung, L., "Silage Temperatures: How Hot is Too Hot?", Jul. 2011, 2 pages (2011).

Hu et al., "Short communication: In vitro ruminal fermentability of a modified corn cultivar expressing a thermotolerant a-amylase," J. Dairy Sci., 93:4846-4849 (2010).

Schoonmaker et al., "Effect of feeding corn modified to contain a unique amylase on performance and carcass characteristics of feedlot steers," The Professional Animal Scientist 30 (2014) 561-565.

Response to APHIS/BRS Review for Technical Completeness of Syngenta's petition for a Determination of Non-regulated Status for Corn Event 3272, assigned APHIS No. 05-280-01p (Jan. 10, 2007).

Robert Plamondon, "Save money on chicken feed," Mother Earth News (Jul. 29, 2019).

Leahy et al., "Effects of treating corn silage with alpha-amylase and (or) sorbic acid on beef cattle growth and carcass characteristics," J. Anim. Sci. (1990), 68: pp. 490-497.

Miller et al., "Effect of altering the physical form of corn silage on utilization by dairy cattle," Journal of Dairy Science, vol. 52, No. 12, pp. 1955-1960.

Syngenta Seeds, Inc. Alpha-Amylase Maize Event 3272, OECD Unique Identifier SYN-E3272-5, Final Environmental Assessment, Feb. 2011, USDA APHIS.

DD2008-70: Determination of the Safety of Syngenta Seeds Inc.'s Corn (*Zea mays* L. (Linnaeus)) Event 3272, Canadian Food Inspection Agency, Mar. 2008.

Determination of Nonregulated Status for Syngenta Seeds Event 3272 Corn (Alpha-amylase and phosphomannose isomerase corn), Animal and Plant Health Inspection Service, U.S. Department of Agriculture, Feb. 11, 2011.

National Environmental Policy Act Decision and Finding of No Significant Impact; Syngenta Seeds, Inc.; Alpha-Amylase Maize Event 3272; USDA, APHIS Biotechnology Regulatory Services dated Feb. 11, 2011.

Meale et al., "Board-Invited Review: Opportunities and challenges in using exogenous enzymes to improve ruminant production," Journal of Animal Science (2014), vol. 92: pp. 427-442.

Extended European Search Report for EP Application No. 18866057.5 dated Jun. 22, 2021.

International Search Report and Written Opinion for International Application No. PCT/US2018/055169 dated Jan. 9, 2019.

Tricarico et al., "Effects of a dietary *Aspergillus oryzae* extract containing—amylase activity on performance and carcass characteristics of finishing beef cattle," Journal of Animal Science, Nov. 22, 2006.

* cited by examiner

* % of DM ** % of Starch

* NIR data ** Analytical chemistry data for combined glucose, fructose, sucrose, lactose and mannitol

ANIMAL FEED COMPOSITIONS AND METHODS OF USE

RELATED APPLICATION INFORMATION

This application is a national stage entry under 35 U.S.C. § 371 of International Application No. PCT/US2018/055169, filed 10 Oct. 2018, which claims the benefit of U.S. Application No. 62/571,378, filed 12 Oct. 2017, the contents of which are incorporated herein by reference in their entirety.

STATEMENT REGARDING ELECTRONIC SUBMISSION OF A SEQUENCE LISTING

A Sequence Listing in ASCII text format, submitted under 37 C.F.R. § 1.821, entitled "81471-US-Seq_Listing_ST25.txt", 15,179 bytes in size, generated on Oct. 8, 2018 and filed via EFS-Web is provided in lieu of a paper copy. This Sequence Listing is hereby incorporated by reference into the specification for its disclosures.

FIELD OF THE INVENTION

The present invention relates to animal feed compositions and methods of using the same for enhancing animal performance and/or the efficiency of feed utilization.

BACKGROUND OF THE INVENTION

Animal feeds can be classified into two groups: (1) concentrates or compound feeds and (2) roughages. Concentrates or compound feeds are high in energy value, including fat, cereal grains and their by-products (barley, corn, oats, rye, wheat), high-protein oil meals or cakes (soybean, canola, cottonseed, peanut and the like), and by-products from processing of sugar beets, sugarcane, animals, and fish, which can be produced in the form of pellets or crumbles. Concentrates or compound feeds can be complete in that they can provide all the daily required food needs or they can provide a part of the ration, supplementing whatever else may be provided as a food ration. Roughage includes pasture grasses, hays, silage, root crops, straw, and stover (cornstalks).

Feed constitutes the largest cost of raising animals for food production. Thus, the present invention is directed to compositions and methods for improving animal performance and/or the efficiency of animal feed utilization, thereby reducing the cost of production.

SUMMARY OF THE INVENTION

One aspect of the present invention provides an animal feed composition comprising microbial α-amylase. In some aspects, the microbial α-amylase comprises a polypeptide having at least about 80% identity to the amino acid sequence of SEQ ID NO:1 or a polypeptide encoded by a nucleotide sequence having at least about 80% identity to the nucleotide sequence of SEQ ID NO:2, SEQ ID NO:3, SEQ ID NO:4 and/or SEQ ID NO:5.

Another aspect of the present invention provides an animal feed composition comprising plant material, wherein the plant material comprises an expressed heterologous α-amylase. In some particular embodiments, the expressed heterologous α-amylase is encoded by a nucleotide sequence having at least about 80% identity to the nucleotide sequence of SEQ ID NO:2, SEQ ID NO:3, SEQ ID NO:4 and/or SEQ ID NO:5 or comprises a polypeptide having at least about 80% identity to the amino acid sequence of SEQ ID NO:1.

The present invention further provides an animal feed composition comprising plant material from a transgenic plant or plant part comprising a recombinant α-amylase encoded by a nucleotide sequence having at least about 80% identity to the nucleotide sequence of SEQ ID NO:2, SEQ ID NO:3, SEQ ID NO:4 and/or SEQ ID NO:5 or comprising a polypeptide having at least about 80% identity to the amino acid sequence of SEQ ID NO:1.

In other aspects, the present invention provides a corn ration comprising plant material from a transgenic corn plant or plant part stably transformed with a recombinant α-amylase encoded by a nucleotide sequence having at least about 80% identity to the nucleotide sequence of SEQ ID NO:2, SEQ ID NO:3, SEQ ID NO:4 and/or SEQ ID NO:5. Additional aspects of the invention provide an animal feed composition comprising the corn ration of the invention.

The invention also encompasses a maize silage comprising transgenic maize plant material comprising a polynucleotide encoding a recombinant α-amylase (as described herein).

A further aspect of the invention provides a method of increasing the average daily weight gain of an animal, comprising feeding to the animal an animal feed composition of the present invention, optionally wherein the average daily weight gain of the animal is increased by about 0.05 lbs/day to about 10 lbs/day. Optionally, the animal is an animal being raised for meat, for example, beef cattle. In embodiments, the beef cattle is a feed lot animal. In embodiments, the animal is growing beef calf (e.g., a backgrounder/stocker animal).

An additional aspect of the invention provides a method of increasing the growth rate (weight gain) of an animal, comprising feeding to the animal an animal feed composition of the present invention, optionally wherein the growth rate of the animal is increased by about 0.05 lb/day to about 10 lbs/day. Optionally, the animal is an animal being raised for meat, for example, beef cattle. In embodiments, the beef cattle is a feed lot animal. In embodiments, the animal is growing beef calf (e.g., a backgrounder/stocker animal).

A still further aspect of the invention provides a method for reducing the number of days needed to achieve a desired weight in an animal, comprising feeding to the animal an animal feed composition of the present invention, thereby reducing the number of days needed to achieve a desired weight.

In other aspects, a method of increasing the efficiency of feed utilization by an animal is provided, the method comprising feeding to the animal an animal feed composition of the present invention in an amount effective to increase the efficiency of feed utilization (e.g., for meat, milk, egg and/or wool production) by the animal. Optionally, the animal is an animal being raised for meat, for example, beef cattle. In embodiments, the beef cattle is a feed lot animal. In embodiments, the animal is growing beef calf (e.g., a backgrounder/stocker animal). In embodiments, the animal is a dairy animal.

The invention further contemplates a method of increasing the amount (e.g., as determined by weight and/or volume) of milk produced by a dairy animal, the method comprising feeding to the dairy animal an animal feed composition of the invention in an amount effective to increase the amount of milk produced by the dairy animal. In embodiments, the dairy animal is a dairy cow or a dairy goat.

In further aspects, the invention provides a method of increasing the efficiency of feed utilization for milk production by a dairy animal, the method comprising feeding to the animal, in an amount effective to increase the efficiency of feed utilization by the dairy animal, an animal feed composition of the invention.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION OF THE INVENTION

Figure 1:
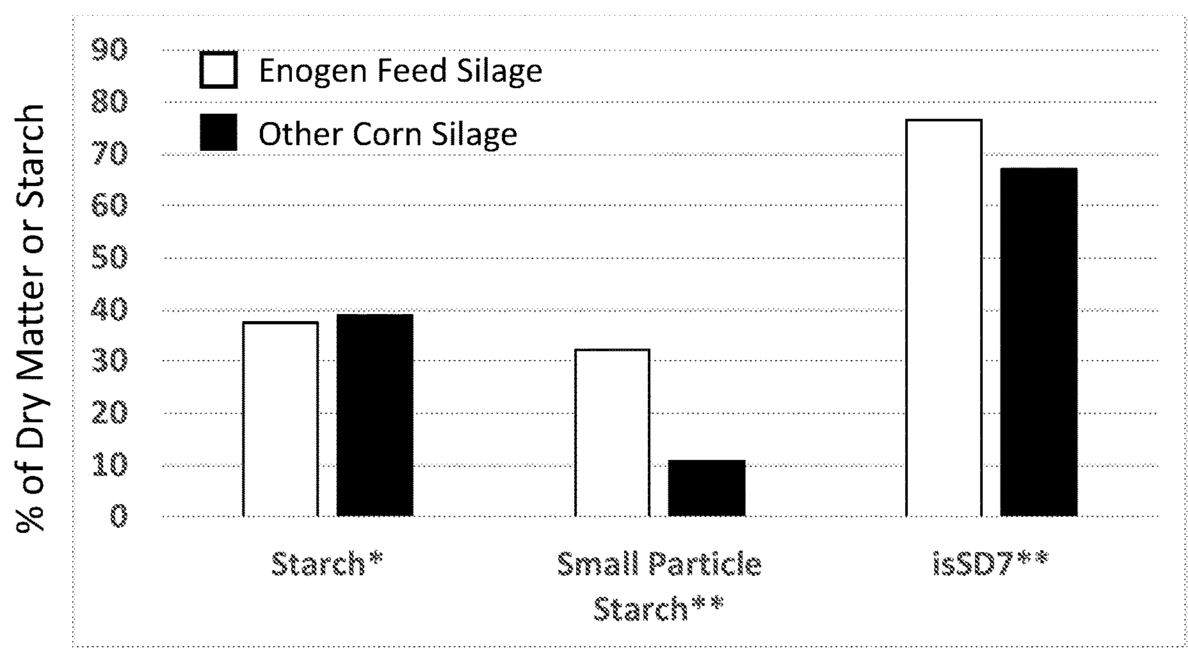
FIG. 1 is a bar graph showing characteristics of Enogen® Feed silage as compared with silage from corn not containing an alpha amylase trait. Total starch ("Starch"), small particle starch (can diffuse through a 50 μM pore), and 7 hour in situ starch digestibility in the rumen ("isSD7"; starch disappearance during 7 hours in the rumen) were determined by analytical chemistry.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage, an amount or a time period and the like, is meant to encompass variations of ±20%, ±10%, ±5%, ±1%, ±0.5%, or even ±0.1% of the specified amount (e.g., an amount of weight gained or feed provided).

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The present invention is directed to compositions and methods for improving animal performance (e.g., increased efficiency of animal feed utilization, increased weight gain in animals raised for meat, increased milk production in dairy animals, increased egg production in poultry and/or increased wool or hair production in animals raised for their wool or hair), thereby reducing the cost of production. The present inventors have made the surprising discovery that animals fed an animal feed composition comprising microbial α-amylase can have an increase in the average daily weight gain or growth rate, an increase in milk production, an increase in the efficiency of feed utilization, an increase in egg production, an increase in wool or hair production and/or a reduction in the number of days required to achieve a desired weight as compared to animals not fed the animal feed composition.

Accordingly, in one aspect of the invention, an animal feed composition comprising microbial α-amylase is provided. In further aspects of the invention, the microbial α-amylase comprises a polypeptide having at least 80% identity to the amino acid sequence of SEQ ID NO:1 or a polypeptide encoded by a nucleotide sequence having at least 80% identity to the nucleotide sequence of SEQ ID NO:2, SEQ ID NO:3, SEQ ID NO:4 and/or SEQ ID NO:5. In some embodiments, the α-amylase is a liquid. Thus, in some embodiments of the invention, an animal feed composition of the invention can be a supplement that comprises a liquid microbial α-amylase that can be added to the feed provided to an animal.

In another aspect, the present invention provides an animal feed composition comprising plant material, wherein the plant material comprises an expressed recombinant α-amylase. In some particular embodiments, the expressed recombinant α-amylase is encoded by a nucleotide sequence having at least about 80% identity to the nucleotide sequence of SEQ ID NO:2, SEQ ID NO:3, SEQ ID NO:4 and/or SEQ ID NO:5 or comprises a polypeptide having at least about 80% identity to the amino acid sequence of SEQ ID NO:1. Thus, in further embodiments, the invention provides an animal feed composition comprising plant material from a transgenic plant or plant part comprising a recombinant α-amylase encoded by a nucleotide sequence having at least about 80% identity to the nucleotide sequence of SEQ ID NO:2, SEQ ID NO:3, SEQ ID NO:4 and/or SEQ ID NO:5 or comprising a polypeptide having at least about 80% identity to the amino acid sequence of SEQ ID NO:1.

In particular embodiments, the transgenic plant or plant part can comprise about 1% to about 100% by weight of the plant material. Thus, for example, the transgenic plant or plant part can comprise about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight of the plant material, and the like, or any range therein. Thus, in some embodiments, the plant material can comprise one or more different types of plants. Thus, for example, the plant material can be from a plant in which recombinant or heterologous (e.g., microbial) α-amylase is expressed. In other embodiments, the plant material comprises, consists essentially of, or consists of material from a plant in which recombinant or heterologous (e.g., microbial) α-amylase is expressed and material from a plant not expressing the recombinant or heterologous α-amylase (e.g., a commodity plant). Thus, in some embodiments, when the plant material comprises material from a plant in which recombinant or heterologous (e.g., microbial) α-amylase is expressed and material from a plant not expressing the recombinant or heterologous α-amylase (e.g., a commodity plant), the material from a plant in which recombinant or heterologous (e.g., microbial) α-amylase is expressed can comprise from about 1% to about 99% by weight of the plant material and the material from a plant not expressing the recombinant or heterologous α-amylase can comprise from about 99% to about 1% by weight of the plant material.

In further embodiments, plant material can comprise from about 5% to about 100% by weight of the animal feed composition. Thus, for example, the plant material can comprise about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight of the animal feed composition, and the like, and/or any range therein.

The animal feed of the invention can be in any form that is useful with this invention. Thus, in some embodiments, the form of the animal feed can be, but is not limited to, pellets, grain including one or more types of grain mixed (i.e., mixed grain), a mixture of grain and pellets, silage, dry-rolled, steam flaked, whole kernel, coarsely cracked kernels (e.g., coarsely cracked corn), high moisture corn and/or any combination thereof. In some embodiments, the animal feed can comprise other components, including but not limited to coarsely cracked kernels, wet distillers grain, dry distillers grain, corn silage, supplements/liquid supplements, corn gluten feed, and/or ground hay.

As used herein, the term "plant material" includes any plant part, including but not limited to endosperm, embryos (germ), pericarp (bran coat), pedicle (tip cap), pollen, ovules, seeds (grain), leaves, flowers, branches, stems, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. Further, as used herein, "plant cell" refers to a structural and physiological unit of the plant, which comprises a cell wall and also may refer to a protoplast. A plant cell of the invention can be in the form of an isolated single cell or can be a cultured cell or can be a part of a higher-organized unit such as, for example, a plant tissue or a plant organ. A "protoplast" is an isolated plant cell without a cell wall or with only parts of the cell wall. Thus, in some embodiments of the invention, a transgenic plant or plant part comprising a recombinant α-amylase encoded by a nucleotide sequence of the invention comprises a cell comprising the recombinant α-amylase encoded by a nucleotide sequence of the invention, wherein the cell is a cell of any plant or plant part including, but not limited to, a root cell, a leaf cell, a tissue culture cell, a seed cell, a flower cell, a fruit cell, a pollen cell, and the like. In representative embodiments, the plant material can be a seed or grain.

The plant material can be from any plant. In some embodiments, the plant material is from a plant in which recombinant or heterologous (e.g., microbial) α-amylase can be expressed. Further, as discussed herein, in other embodiments, the plant material can be a mixture of plant material from a plant in which recombinant or heterologous (e.g., microbial) α-amylase is expressed and from a plant not expressing the recombinant or heterologous α-amylase (e.g., a commodity plant). Thus, in representative embodiments, the plant material can be a mixture of normal "commodity" plant material (e.g., commodity corn) and plant material from a transgenic plant of the present invention expressing recombinant or heterologous α-amylase.

Thus, in some embodiments, the plant material can be from a corn plant, a sorghum plant, a wheat plant, a barley plant, a rye plant, an oat plant, a rice plant, and/or a millet plant. In representative embodiments, the plant material can be from a corn plant. In other embodiments, the plant material can be a seed, kernel or grain from a corn plant. In embodiments, the plant material can be from a corn plant expressing a thermostable alpha amylase, for example, alpha amylase 797GL3 or D45. Alpha amylase 797GL3 is described in U.S. Patent Publication US2010/0240082 (as SEQ ID NO: 1) and in Richardson et al., (2002) *J. Biol. Chem.* 277: 26501-26507. Alpha amylase D45 has been described in U.S. Patent Publication US2010/0240082 (as SEQ ID NO: 2) and by Atichokudomchai et al. (2006) *Carbohydrate Polymers* 64:582-588. In particular embodiments, the plant material can be from a corn plant comprising corn event 3272 (see, U.S. Pat. No. 8,093,453). In embodiments, the alpha amylase is not a thermostable amylase. In embodiments, the alpha amylase can tolerate a wide pH range (e.g., is active across a wide pH range, including acidic pH). In representative embodiments, the animal feed is a corn silage comprising a polynucleotide encoding an alpha amylase that is thermostable and/or is active over a wide range of pH values, for example alpha amylase 797GL3 and/or D45. Without wishing to be bound by any particular theory of the invention, the process of chopping up corn plant material prior to ensiling may activate a thermostable enzyme. Further, an alpha amylase that is active over a wide range of pH (e.g., including in the acidic range) can be advantageous in the production of silage because the pH of the plant material will decrease as fermentation progresses.

When the plant material is a silage (e.g., a corn silage), the silage can optionally be fermented in the presence of a microbial inoculant and/or chemical stabilizer. It is known in the art that an inoculant, such as lactic acid bacteria, and/or a chemical stabilizer can increase aerobic stability of the silage and thereby reduce spoilage. Examples of suitable inoculants include without limitation homofermentative and/or heterofermentative lactic acid bacteria such as: *Lactobacillus* spp. (e.g., *L. buchneri, L. plantarum, L. casei, L. brevis* and/or *L. acidophilus*), *Pediococcus* spp. (e.g., *P. pentosaceus* and/or *P. acidilactici*), *Lactococcus* spp. *Enterococcus* spp (e.g., *E. faecium*). *Streptococcus* spp. and/or *Leuconostoc* spp. A commercially available inoculant, designated LB500, is available from Lallemand Animal Nutrition. Chemical stabilizers include without limitation organic and/or mineral acids (e.g., acetic acid, formic acid, butyric acid, lactic acid, propionic acid, volatile fatty acids, sulfuric acid and/or hydrochloric acid), sodium chloride, sodium bicarbonate, sucrose and/or urea, and the like. Thus, in embodiments, the silage comprises a microbial inoculant and/or chemical stabilizer. Further, it is known in the art that kernel processing (e.g., cracked corn) prior to ensiling increases the nutritive value of corn silage. However, kernel processing may slow down the rate of harvesting/ensiling and consumes energy, and thereby may incur additional expense. In embodiments, the corn silage of the invention (e.g., prepared from a transgenic corn plant expressing alpha amylase) can achieve the same or better nutritive value than conventional corn silage (without exogenous alpha amylase) and/or can support the same or better level of animal performance (e.g., milk production, meat production, and the like) with no kernel processing or reduced kernel processing than the conventional corn silage. Thus, in embodiments, the corn silage of the invention is made from corn plants with no or essentially no kernel processing or reduced kernel processing than is conventionally used in the industry. In embodiments, the kernels are processed to be larger than about 2 mm (e.g., at least 3 mm or larger, 4 mm or larger, 5 mm or larger, 6 mm or larger, 7 mm or larger, 8 mm or larger, 9 mm or later, 10 mm or larger, and the like).

In some embodiments, the invention provides a "total mixed ration" comprising the animal feed. In embodiments, the total mixed ration comprises an animal feed comprising plant material from a transgenic plant (e.g., transgenic corn plant) or plant part stably transformed with a recombinant α-amylase, optionally encoded by a nucleotide sequence having about 80% identity to the nucleotide sequence of SEQ ID NO:2, SEQ ID NO:3, SEQ ID NO:4 and/or SEQ ID NO:5 and/or comprising a polypeptide having at least about 80% identity to the amino acid sequence of SEQ ID NO:1. As used herein, "total mixed ration" refers to a ration that combines all feedstuffs (e.g., grains, roughage/forage, proteins, mineral, vitamins and/or feed additives, and the like) into a complete ration formulated to a specific nutrient concentration in a single feed mix, often calculated based on the 24 hour nutritional needs for an individual animal. In embodiments, the total mixed ration includes, for example, corn grain (e.g., corn kernels, coarsely cracked corn, and the like), supplements and additives, (e.g., vitamins and minerals), and/or "roughages" (e.g., pasture grasses, hays, silage, root crops, straw, and stover (cornstalks)). In embodiments, the corn grain (e.g., corn grain) and/or roughage (e.g., corn silage) component is from transgenic plant material (e.g., transgenic corn plant material) and comprises a polynucleotide encoding the alpha amylase.

In some embodiments, the plant material from a transgenic corn plant or plant part (e.g., corn grain and/or corn silage) comprises from about 1% to about 100% by weight on a dry matter basis of the total mixed ration. Thus, for example, the transgenic plant or plant part can comprise at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or even 100% by weight on a dry matter basis of the plant material, and the like, and/or any range therein.

In still further embodiments, the invention provides a corn ration comprising plant material from a transgenic corn plant or plant part stably transformed with a recombinant α-amylase, optionally encoded by a nucleotide sequence having about 80% identity to the nucleotide sequence of SEQ ID NO:2, SEQ ID NO:3, SEQ ID NO:4 and/or SEQ ID NO:5 and/or comprising a polypeptide having at least about 80% identity to the amino acid sequence of SEQ ID NO:1. As used herein, "corn ration" means the corn allowance (e.g., 24 hour corn allowance) for an individual animal.

In some embodiments, the plant material from a transgenic corn plant or plant part comprises from about 1% to about 100% by weight on a dry matter basis of the corn ration. Thus, for example, the transgenic plant or plant part can comprise at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or even 100% by weight on a dry matter basis of the plant material, and the like, and/or any range therein.

In other embodiments, an animal feed composition is provided that comprises a corn ration of the invention. In some embodiments, the corn ration can comprise about 5% to about 100% by weight on a dry matter basis of the animal feed composition. Thus, for example, the corn ration can comprise at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% by weight on a dry matter basis of the animal feed composition, and the like, and/or any range therein. In representative embodiments, the animal feed composition comprises at least about 50%.

In some embodiments, the total mixed ration can comprise wet corn gluten feed that can be about 10% to about 40% by weight on a dry matter basis of the animal feed composition. In further embodiments the total mixed ration can comprise wet corn gluten feed that can be at least about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or more by weight on a dry matter basis of the animal feed composition.

In other embodiments, the total mixed ration can comprise modified distillers grains with solubles that can be about 5% to about 25% by weight on a dry matter basis of the animal feed composition. In further embodiments the total mixed ration can comprise modified distillers grains with solubles that can be at least about 5%, 6%, 7%, 8%, 9%, 10%, 11%, 12%, 13%, 14%, 15%, 16%, 17%, 18%, 19%, 20%, 21%, 22%, 23%, 24%, 25%, by weight on a dry matter basis of the animal feed composition.

In further embodiments, the total mixed ration can comprise wet distillers grains with solubles that can be about 5% to about 25% by weight on a dry matter basis of the animal feed composition. In further embodiments the total mixed ration can comprise wet distillers grains with solubles that can be at least about 5%, 6%, 7%, 8%, 9%, 10%, 11%, 12%, 13%, 14%, 15%, 16%, 17%, 18%, 19%, 20%, 21%, 22%, 23%, 24%, 25%, by weight on a dry matter basis of the animal feed composition.

Further, in the case of transgenic corn plant material expressing the alpha amylase, the total corn grain ration can comprise all or essentially all transgenic corn plant material expressing the alpha amylase, or only a portion of the corn grain ration can come from a transgenic corn plant expressing the alpha amylase, e.g., at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight on a dry matter basis of the corn grain ration is from a transgenic corn plant comprising a polynucleotide encoding the alpha amylase. The remaining portion of the corn grain ration can come from any other suitable source, including without limitation, conventional corn grain not expressing an alpha amylase.

In embodiments, the roughage/forage fed to the animal comprises a corn silage. The animal's daily roughage ration can comprise all or essentially all silage from transgenic corn plant material, or only a portion of the roughage ration can be silage from a transgenic corn plant expressing the alpha amylase, e.g., at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight on a dry matter basis of the roughage ration is silage from a transgenic corn plant comprising a polynucleotide encoding the alpha amylase. The remaining portion of the roughage component can be from any suitable source, including without limitation, conventional corn silage not expressing an alpha amylase, other conventional silages (e.g., alfalfa silage), pasture grass, and the like.

In embodiments, at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or even 100% by weight on a dry matter basis of the corn silage fed to the animal is from a transgenic maize plant comprising a polynucleotide encoding the alpha amylase.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention (e.g., SEQ ID NO:1, SEQ ID NO:2, SEQ ID NO:3, SEQ ID NO:4, SEQ ID NO:5). "Orthologous," as used herein, refers to homologous nucleotide sequences and/or amino acid sequences in different species that arose from a common ancestral gene during speciation. A homologue of this invention has a significant sequence identity (e.g., 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to SEQ ID NO:1, SEQ ID NO:2, SEQ ID NO:3, SEQ ID NO:4 or SEQ ID NO:5.

A homologue of SEQ ID NO:1, SEQ ID NO:2, SEQ ID NO:3, SEQ ID NO:4 and/or SEQ ID NO:5 can be utilized with any feed composition or method of the invention, alone or in combination with one another and/or with SEQ ID NO:1, SEQ ID NO:2, SEQ ID NO:3, SEQ ID NO:4 and/or SEQ ID NO:5.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

The phrase "substantially identical," in the context of two nucleic acid molecules, nucleotide sequences or protein sequences, refers to two or more sequences or subsequences that have at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 95%, at least about 96%, at least about 97%, at least about 98%, or at least about 99% nucleotide or amino acid residue identity, when compared and aligned for maximum correspondence, as measured using one of the following sequence comparison algorithms, described herein and as known in the art, or by visual inspection. In some embodiments of the invention, the substantial identity exists over a region of the sequences that is at least about 50 residues to about 200 residues, about 50 residues to about 150 residues, and the like, in length. Thus, in some embodiments of the invention, the substantial identity exists over a region of the sequences that is at least about 50, about 60, about 70, about 80, about 90, about 100, about 110, about 120, about 130, about 140, about 150, about 160, about 170, about 180, about 190, about 200, or more residues in length. In a further embodiment, the sequences are substantially identical over the entire length of the coding regions. Furthermore, in representative embodiments, substantially identical nucleotide or protein sequences perform substantially the same function (e.g., α-amylase activity). Thus, in some particular embodiments, the sequences are substantially identical over at least about 150 residues and have α-amylase activity.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially identical when the two sequences hybridize to each other under stringent conditions. In some representative embodiments, two nucleotide sequences considered to be substantially identical hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or Northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× or higher than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences (e.g., SEQ ID NO:2, SEQ ID NO:3, SEQ ID NO:4, SEQ ID NO:5). In one embodiment, a reference nucleotide sequence hybridizes to the "test" nucleotide sequence in 7% sodium dodecyl sulfate (SDS), 0.5 M $NaPO_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M $NaPO_4$, 1 mM EDTA at 50° C. with washing in 1×SSC, 0.1% SDS at 50° C. or in 7% sodium dodecyl sulfate (SDS), 0.5 M $NaPO_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M $NaPO_4$, 1 mM EDTA at 50° C. with washing in 0.1×SSC, 0.1% SDS at 50° C., or in 7% sodium dodecyl sulfate (SDS), 0.5 M $NaPO_4$, 1 mM EDTA at 50° C. with washing in 0.1×SSC, 0.1% SDS at 65° C.

In particular embodiments, a further indication that two nucleotide sequences or two polypeptide sequences are substantially identical can be that the protein encoded by the first nucleic acid is immunologically cross reactive with, or specifically binds to, the protein encoded by the second nucleic acid. Thus, in some embodiments, a polypeptide can be substantially identical to a second polypeptide, for example, where the two polypeptides differ only by conservative substitutions.

Accordingly, in some embodiments of the invention, nucleotide sequences having significant sequence identity to the nucleotide sequence of SEQ ID NO:2, SEQ ID NO:3, SEQ ID NO:4 and/or SEQ ID NO:5 are provided. "Significant sequence identity" or "significant sequence similarity" means at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100% identity or similarity with another nucleotide sequence. Thus, in additional embodiments, "significant sequence identity" or "significant sequence similarity" means a range of about 70% to about 100%, about 75% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, and/or about 99% to about 100% identity or similarity with another nucleotide sequence. Therefore, in some embodiments, a nucleotide sequence of the invention is a nucleotide sequence that has significant sequence identity to the nucleotide sequence of SEQ ID NO:2, SEQ ID NO:3, SEQ ID NO:4 or SEQ ID NO:5 and encodes a polypeptide having α-amylase activity. In some embodiments, a nucleotide sequence of the invention is a nucleotide sequence that has 80% to 100% identity to the nucleotide sequence of SEQ ID NO:2, SEQ ID NO:3, SEQ ID NO:4 or SEQ ID NO:5 and encodes a polypeptide having α-amylase activity. In representative embodiments, a nucleotide sequence of the invention is a nucleotide sequence that has 95% identity to the nucleotide sequence of SEQ ID NO:2, SEQ ID NO:3, SEQ ID NO:4 or SEQ ID NO:5 and encodes a polypeptide having α-amylase activity.

In some embodiments, a polypeptide of the invention comprises, consists essentially of, or consists of an amino acid sequence that is at least 70% identical, e.g., at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100% identical to the amino acid sequence of SEQ ID NO:1 and has a amylase activity.

In some embodiments, a polypeptide or nucleotide sequence can be a conservatively modified variant. As used herein, "conservatively modified variant" refer to polypeptide and nucleotide sequences containing individual substitutions, deletions or additions that alter, add or delete a single amino acid or nucleotide or a small percentage of amino acids or nucleotides in the sequence, where the alteration results in the substitution of an amino acid with a chemically similar amino acid. Conservative substitution tables providing functionally similar amino acids are well known in the art.

As used herein, a conservatively modified variant of a polypeptide is biologically active and therefore possesses the desired activity of the reference polypeptide (e.g., α-amylase activity) as described herein. The variant can result from, for example, a genetic polymorphism or human manipulation. A biologically active variant of the reference polypeptide can have at least about 40%, 45%, 50%, 55%, 60%, 65%, 70%, 75%, 80%, 85%, 90%, 91%, 92%, 93%, 94%, 95%, 96%, 97%, 98%, 99%, or more sequence identity or similarity (e.g., about 40% to about 99% or more sequence identity or similarity and any range therein) to the amino acid sequence for the reference polypeptide as determined by sequence alignment programs and parameters described elsewhere herein. An active variant can differ from the reference polypeptide sequence by as few as 1-15 amino acid residues, as few as 1-10, such as 6-10, as few as 5, as few as 4, 3, 2, or even 1 amino acid residue.

Naturally occurring variants may exist within a population. Such variants can be identified by using well-known molecular biology techniques, such as the polymerase chain reaction (PCR), and hybridization as described below. Synthetically derived nucleotide sequences, for example, sequences generated by site-directed mutagenesis or PCR-mediated mutagenesis which encode a polypeptide of the invention, are also included as variants. One or more nucleotide or amino acid substitutions, additions, or deletions can be introduced into a nucleotide or amino acid sequence disclosed herein, such that the substitutions, additions, or deletions are introduced into the encoded protein. The additions (insertions) or deletions (truncations) may be made at the N-terminal or C-terminal end of the native protein, or at one or more sites in the native protein. Similarly, a substitution of one or more nucleotides or amino acids may be made at one or more sites in the native protein.

For example, conservative amino acid substitutions may be made at one or more predicted preferably nonessential amino acid residues. A "nonessential" amino acid residue is a residue that can be altered from the wild-type sequence of a protein without altering the biological activity, whereas an "essential" amino acid is required for biological activity. A "conservative amino acid substitution" is one in which the amino acid residue is replaced with an amino acid residue with a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, where such residues are essential for protein activity.

For example, amino acid sequence variants of the reference polypeptide can be prepared by mutating the nucleotide sequence encoding the enzyme. The resulting mutants can be expressed recombinantly in plants, and screened for those that retain biological activity by assaying for α-amylase activity using methods well known in the art. Methods for mutagenesis and nucleotide sequence alterations are known in the art. See, e.g., Kunkel (1985) *Proc. Natl. Acad. Sci. USA* 82:488-492; Kunkel et al. (1987) *Methods in Enzymol.* 154:367-382; and *Techniques in Molecular Biology* (Walker & Gaastra eds., MacMillan Publishing Co. 1983) and the references cited therein; as well as U.S. Pat. No. 4,873,192. Clearly, the mutations made in the DNA encoding the variant must not disrupt the reading frame and preferably will not create complimentary regions that could produce secondary mRNA structure. See, EP Patent Application Publication No. 75,444. Guidance as to appropriate amino acid substitutions that do not affect biological activity of the protein of interest may be found in the model of Dayhoff et al. (1978) *Atlas of Protein Sequence and Structure* (National Biomedical Research Foundation, Washington, D.C.), herein incorporated by reference.

The deletions, insertions and substitutions in the polypeptides described herein are not expected to produce radical changes in the characteristics of the polypeptide (e.g., the activity of the polypeptide). However, when it is difficult to predict the exact effect of the substitution, deletion or insertion in advance of doing so, one of skill in the art will appreciate that the effect can be evaluated by routine screening assays that can screen for the particular polypeptide activities of interest (e.g., α-amylase activity).

In some embodiments, the compositions of the invention can comprise active fragments of the polypeptide. As used herein, "fragment" means a portion of the reference polypeptide that retains the polypeptide activity of α-amylase. A fragment also means a portion of a nucleic acid molecule encoding the reference polypeptide. An active fragment of the polypeptide can be prepared, for example, by isolating a portion of a polypeptide-encoding nucleic acid molecule that expresses the encoded fragment of the polypeptide (e.g., by recombinant expression in vitro), and assessing the activity of the fragment. Nucleic acid molecules encoding such fragments can be at least about 150, 200, 250, 300, 350, 400, 450, 500, 550, 600, 650, 700, 800, 900, 1000, 1100, 1200, 1300, 1400, 1500, 1600, 1700, 1800, 1900, 2000, 2100, or 2200 contiguous nucleotides, or any range therein, or up to the number of nucleotides present in a full-length polypeptide-encoding nucleic acid molecule. As such, polypeptide fragments can be at least about 50, 60, 70, 80, 90, 100, 125, 150, 175, 200, 225, 250, 275, 300, 325, 350, 375, 400, 425, 450, 475, 500, 525, 550, 525, 550, 600, 625, 650, 675, or 700 contiguous amino acid residues, or any range therein, or up to the total number of amino acid residues present in the full-length polypeptide. Thus, in some embodiments, the invention provides a polypeptide comprising, consisting essentially of, or consisting of at least about 150 contiguous amino acid residues of a polypeptide of the invention (e.g., SEQ ID NO:1) and having α-amylase activity.

As used herein, the terms "express," "expresses," "expressed" or "expression," and the like, with respect to a nucleic acid molecule and/or a nucleotide sequence (e.g., RNA or DNA) indicates that the nucleic acid molecule and/or nucleotide sequence is transcribed and, optionally, translated. Thus, a nucleic acid molecule and/or nucleotide sequence may express or produce a polypeptide of interest or a functional untranslated RNA.

A "heterologous" or "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid sequence is a nucleotide sequence naturally associated with a host cell into which it is introduced.

Also as used herein, the terms "nucleic acid," "nucleic acid molecule," "nucleotide sequence" and "polynucleotide" can be used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

In some embodiments, the recombinant nucleic acids molecules, nucleotide sequences and polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the recombinant nucleic acid molecules, nucleotide sequences and their encoded polypeptides are "isolated" in that, by the hand of man, they exist apart from their native environment and therefore are not products of nature, however, in some embodiments, they can be introduced into and exist in a recombinant host cell.

In some embodiments, the nucleotide sequences and/or nucleic acid molecules of the invention can be operatively associated with a variety of promoters for expression in host cells (e.g., plant cells). As used herein, "operatively associated with," when referring to a first nucleic acid sequence that is operatively linked to a second nucleic acid sequence, means a situation when the first nucleic acid sequence is placed in a functional relationship with the second nucleic acid sequence. For instance, a promoter is operatively associated with a coding sequence if the promoter effects the transcription or expression of the coding sequence.

A DNA "promoter" is an untranslated DNA sequence upstream of a coding region that contains the binding site for RNA polymerase and initiates transcription of the DNA. A "promoter region" can also include other elements that act as regulators of gene expression. Promoters can include, for example, constitutive, inducible, temporally regulated, developmentally regulated, chemically regulated, tissue-preferred and tissue-specific promoters for use in the preparation of recombinant nucleic acid molecules, i.e., chimeric genes. In particular aspects, a "promoter" useful with the invention is a promoter capable of initiating transcription of a nucleotide sequence in a cell of a plant.

A "chimeric gene" is a recombinant nucleic acid molecule in which a promoter or other regulatory nucleotide sequence is operatively associated with a nucleotide sequence that codes for an mRNA or which is expressed as a protein, such that the regulatory nucleotide sequence is able to regulate transcription or expression of the associated nucleotide sequence. The regulatory nucleotide sequence of the chimeric gene is not normally operatively linked to the associated nucleotide sequence as found in nature.

The choice of promoter will vary depending on the temporal and spatial requirements for expression, and also depending on the host cell to be transformed. Thus, for example, expression of a nucleotide sequence can be in any plant and/or plant part, (e.g., in leaves, in stalks or stems, in ears, in inflorescences (e.g., spikes, panicles, cobs, etc.), in roots, seeds and/or seedlings, and the like). Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Promoters useful with the invention include, but are not limited to, those that drive expression of a nucleotide sequence constitutively, those that drive expression when induced, and those that drive expression in a tissue- or developmentally-specific manner. These various types of promoters are known in the art.

Examples of constitutive promoters include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *Arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. Further, the promoter expression cassettes described by McElroy et al. (*Mol. Gen. Genet.* 231: 150-160 (1991)) can be easily modified for the expression of nucleotide sequences and are particularly suitable for use in monocotyledonous hosts.

In some embodiments, tissue specific/tissue preferred promoters can be used. Tissue specific or preferred expression patterns include, but are not limited to, green tissue specific or preferred, root specific or preferred, stem specific or preferred, seed specific or preferred, and flower specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein (e.g., gamma zein) or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of nucleotide sequences in plants, particularly maize, include but are not limited to those that direct expression in root, pith, leaf or pollen. Such promoters are disclosed, for example, in PCT Publication WO 93/07278, herein incorporated by reference in its entirety. Other non-limiting examples of tissue specific or tissue preferred promoters include the cotton rubisco promoter disclosed in U.S. Pat. No. 6,040,504; the rice sucrose synthase promoter disclosed in U.S. Pat. No. 5,604,121; the root specific promoter described by de Framond (*FEBS* 290:103-106 (1991); EP 0 452 269 to Ciba-Geigy); the stem specific promoter described in U.S. Pat. No. 5,625,136 (to Ciba-Geigy) and which drives expression of the maize trpA gene; and the cestrum yellow leaf curling virus promoter disclosed in PCT Publication WO 01/73087, all incorporated by reference herein.

Additional examples of tissue-specific/tissue preferred promoters include, but are not limited to, the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Particularly useful for seed-specific expression is the pea vicilin promoter (Czako et al. (1992) *Mol. Gen. Genet.* 235:33-40; as well as the seed-specific promoters disclosed in U.S. Pat. No. 5,625,136. In some embodiments, the promoter can be an endosperm-specific promoter including but not limited to a maize gamma-zein promoter or a maize ADP-gpp promoter.

Useful promoters for expression in mature leaves are those that are switched on at the onset of senescence, such as the SAG promoter from *Arabidopsis* (Gan et al. (1995) *Science* 270:1986-1988).

In addition, promoters functional in plastids can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of a gene in a plant through the application of an exogenous chemical regulator. Regulation of the expression of nucleotide sequences via promoters that are chemically regulated enables the polypeptides of the invention to be synthesized only when the crop plants are treated with the inducing chemicals. Depending upon the objective, the promoter may be a chemical-inducible promoter, where application of a chemical induces gene expression, or a chemical-repressible promoter, where application of the chemical represses gene expression.

Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid (e.g., the PR1a system), steroid steroid-responsive promoters (see, e.g., the glucocorticoid-inducible promoter in Schena et al. (1991) *Proc. Natl. Acad. Sci. USA* 88, 10421-10425 and McNellis et al. (1998) *Plant J.* 14, 247-257) and tetracycline-inducible and tetracycline-repressible promoters (see, e.g., Gatz et al. (1991) *Mol. Gen. Genet.* 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters.

Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), and the glyceraldehyde-3-phosphate dehydrogenase promoter (Kohler et al. (1995) *Plant Mol.*

*Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) *Current Opinion Biotechnol.* 7:168-172 and Gatz (1997) *Annu. Rev. Plant Physiol. Plant Mol. Biol.* 48:89-108. Other chemically inducible promoters useful for directing the expression of the nucleotide sequences of this invention in plants are disclosed in U.S. Pat. No. 5,614,395 herein incorporated by reference in its entirety. Chemical induction of gene expression is also detailed in the published application EP 0 332 104 (to Ciba-Geigy) and U.S. Pat. No. 5,614,395. In some embodiments, a promoter for chemical induction can be the tobacco PR-1a promoter.

A polypeptide of this invention may or may not be targeted to a compartment within the plant through use of a signal sequence. Numerous signal sequences are known to influence the expression or targeting of a polynucleotide to a particular compartment/tissue or outside a particular compartment/tissue. Suitable signal sequences and targeting promoters are known in the art and include, but are not limited to, those provided herein (see, e.g., U.S. Pat. No. 7,919,681). Examples of targets include, but are not limited to, the vacuole, endoplasmic reticulum (ER), chloroplast, amyloplast, starch granule, cell wall, seed, or to a particular tissue, e.g., endosperm. Thus, a nucleotide sequence encoding a polypeptide of the invention (e.g., SEQ ID NO:1) can be operably linked to a signal sequence for targeting and/or retaining the polypeptide to a compartment within a plant. In some embodiments, the signal sequence may be an N-terminal signal sequence from waxy, an N-terminal signal sequence from gamma-zein, a starch binding domain, or a C-terminal starch binding domain. In further embodiments, the signal sequence can be an ER signal sequence, an ER retention sequence, an ER signal sequence and an additional ER retention sequence. Thus, in some embodiments of the invention, the α-amylase polypeptides can be fused with one or more signal sequences (and/or nucleotide sequences encoding the polypeptides can be operably linked to nucleotide sequences encoding the signal sequences).

As used herein, "expression cassette" means a nucleic acid molecule comprising a nucleotide sequence of interest (e.g., the nucleotide sequence of SEQ ID NO:2, SEQ ID NO:3, SEQ ID NO:4 and/or SEQ ID NO:5), wherein the nucleotide sequence is operatively associated with at least a control sequence (e.g., a promoter). Thus, some embodiments of the invention provide expression cassettes designed to express the nucleotide sequence of SEQ ID NO:2, SEQ ID NO:3, SEQ ID NO:4 and/or SEQ ID NO:5. In this manner, for example, one or more plant promoters operatively associated with the nucleotide sequence of SEQ ID NO:2, SEQ ID NO:3, SEQ ID NO:4 and/or SEQ ID NO:5 or a nucleotide sequence having substantial identity to the nucleotide sequence of SEQ ID NO:2, SEQ ID NO:3, SEQ ID NO:4 and/or SEQ ID NO:5 can be provided in an expression cassette for expression in an organism or cell thereof (e.g., a plant, plant part and/or plant cell).

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event.

In addition to the promoters operatively linked to a nucleotide sequence to be expressed, an expression cassette can also include other regulatory sequences. As used herein, a "regulatory sequence" means a nucleotide sequence located upstream (5' non-coding sequences), within and/or downstream (3' non-coding sequences) of a coding sequence, and/or which influences the transcription, RNA processing or stability, or translation of the associated coding sequence. Regulatory sequences include, but are not limited to, promoters, enhancers, introns, translation leader sequences, termination signals, and polyadenylation signal sequences. In some embodiments, an expression cassette can also include nucleotide sequences encoding signal sequences operably linked to a polynucleotide sequence of the invention.

For purposes of the invention, the regulatory sequences or regions can be native/analogous to the plant, plant part and/or plant cell and/or the regulatory sequences can be native/analogous to the other regulatory sequences. Alternatively, the regulatory sequences may be heterologous to the plant (and/or plant part and/or plant cell) and/or to each other (i.e., the regulatory sequences). Thus, for example, a promoter can be heterologous when it is operatively linked to a polynucleotide from a species different from the species from which the polynucleotide was derived. Alternatively, a promoter can also be heterologous to a selected nucleotide sequence if the promoter is from the same/analogous species from which the polynucleotide is derived, but one or both (i.e., promoter and/or polynucleotide) are substantially modified from their original form and/or genomic locus, and/or the promoter is not the native promoter for the operably linked polynucleotide.

A number of non-translated leader sequences derived from viruses are known to enhance gene expression. Specifically, leader sequences from Tobacco Mosaic Virus (TMV, the "ω-sequence"), Maize Chlorotic Mottle Virus (MCMV) and Alfalfa Mosaic Virus (AMV) have been shown to be effective in enhancing expression (Gallie et al. (1987) *Nucleic Acids Res.* 15:8693-8711; and Skuzeski et al. (1990) *Plant Mol. Biol.* 15:65-79). Other leader sequences known in the art include, but are not limited to, picornavirus leaders such as an encephalomyocarditis (EMCV) 5' non-coding region leader (Elroy-Stein et al. (1989) *Proc. Natl. Acad. Sci. USA* 86:6126-6130); potyvirus leaders such as a Tobacco Etch Virus (TEV) leader (Allison et al. (1986) *Virology* 154:9-20); Maize Dwarf Mosaic Virus (MDMV) leader (Allison et al. (1986), supra); human immunoglobulin heavy-chain binding protein (BiP) leader (Macejak & Samow (1991) *Nature* 353:90-94); untranslated leader from the coat protein mRNA of AMV (AMV RNA 4; Jobling & Gehrke (1987) *Nature* 325:622-625); tobacco mosaic TMV leader (Gallie et al. (1989) *Molecular Biology of RNA* 237-256); and MCMV leader (Lommel et al. (1991) *Virology* 81:382-385). See also, Della-Cioppa et al. (1987) *Plant Physiol.* 84:965-968.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used.

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) J. Biol. Chem. 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of the invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac," pp. 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin, which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of the invention.

In other aspects of the invention a method of increasing the growth rate (weight gain) or the average daily weight gain of an animal (e.g., an animal being raised for meat production) is provided, the method comprising feeding to the animal an animal feed composition of the present invention. In embodiments, the growth rate of the animal or the average daily weight gain of the animal is increased by about 0.05 lb/day to about 10 lbs/day as compared to the growth rate of a control animal that is not provided the animal feed composition of the invention. Thus, in some embodiments the increase in growth rate or average daily weight gain can be at least about 0.05, 0.06, 0.07, 0.08, 0.09, 0.1, 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.25, 1.5, 1.75, 2, 2.25, 2.5, 2.75, 3, 3.25, 3.5, 3.75, 4, 4.1, 4.2, 4.21, 4.22, 4.23, 4.24, 4.25, 4.26, 4.27, 4.28, 4.29, 4.3, 4.31, 4.32, 4.33, 4.34, 4.35, 4.36, 4.37, 4.38, 4.39, 4.4, 4.41, 4.42, 4.43, 4.44, 4.45, 4.46, 4.47, 4.48, 4.49, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, 10 lbs/day, and the like and/or any range therein. In some particular embodiments, the increase in growth rate or average daily weight gain can be from about 0.05 lb/day to about 0.5 lb/per day. In further embodiments, the increase in growth rate or average daily weight gain can be about 0.1 lb/day as compared to the growth of a control animal that is not provided the animal feed composition.

In still further aspects of the invention, a method for reducing the number of days needed to achieve a desired weight in an animal is provided, the method comprising feeding to the animal an animal feed composition of the invention, thereby reducing the number of days needed to achieve a desired weight as compared to the number of days needed to achieve the same desired weight in a control animal that is not fed the animal feed composition.

As used herein, a "desired weight" "or desired finished weight" can mean a live weight or a hot carcass weight. Thus, for example, for cattle, a desired live weight can be between about 950 to about 1,600 lbs and a desired hot carcass weight can be between about 700 to about 1,000 lbs.

Conventionally, after weaning and prior to entering a feedlot, "backgrounder" beef cattle (also known as "stocker" cattle) spend most of their life grazing on range or pasture land and then are transported to a feedlot for finishing where they are fed grain and other feed concentrates. According to the present invention, however, the methods of the invention can be practiced with backgrounder beef cattle, e.g., a growing beef calf (male and/or female) after weaning, optionally being raised to go to a feedlot for finishing.

Generally, cattle enter a feedlot at a weight of about 600 to about 750 lbs. Depending on weight at placement, the feeding conditions, and the desired finished weight, the period in a feedlot can be in a range from about 90 days to about 300 days. The average gain can be from about 2.5 to about 5 pounds per day.

Accordingly, in another aspect of the invention, the number of days needed to achieve a desired weight in an animal fed the animal feed compositions of the invention can be reduced by about 1 day to about 30 days as compared to a control animal that is not fed the animal feed composition. In some embodiments, the number of days needed to achieve a desired weight in an animal fed the animal feed compositions of the invention can be reduced by about 1 day to about 25 days, about 1 day to about 20 days, about 5 days to about 20 days, about 5 days to about 15 days, and the like, as compared to a control animal that is not fed the animal feed composition. Thus, in some embodiments, the number of days needed to achieve a desired weight in an animal fed an animal feed composition of the invention can reduced by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days and the like and/or any range therein.

In other aspects of the invention, a method of increasing the efficiency of feed utilization by an animal is provided (e.g., for meat, milk, egg and/or wool production), the method comprising feeding to the animal an animal feed composition of the invention in an amount effective to increase the efficiency of feed utilization by the animal as compared to a control animal that is not fed the animal feed composition.

Efficiency of feed utilization can be calculated as dry matter intake divided by the gain in body weight of the animal. In some embodiments, the body weight is the finished body weight prior to slaughter. In further embodiments, the feed provided is the amount of feed that is provided over a period of about 15, 30, 45, 60 or 90 days to about 30, 60, 90, 120, 150, 180, 240, or 300 days, and any range therein as long as the value of the lower range is less than the value of the upper range. In some embodiments the feed provided is the amount of feed that is provided over a period of about 100 days to about 275 days, about 125 days to about 250 days, about 150 days to about 225 days, about 180 days to about 200 days, and the like.

Accordingly, in some embodiments, the time period (number of days) over which the weight gain is measured is 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300 days, and the like, and/or any range therein.

In further aspects of the invention, the feeding value of corn by the animal is increased by about 1% to about 25% as compared to a control animal that is not fed the animal feed composition. The feeding value of corn equals the difference in feed efficiency of the feed composition of the present invention and the feed efficiency of a control animal that is not fed the feed composition, divided by the feed efficiency of the control animal that is not fed the feed composition, all of which is divided by the percent corn inclusion of the feed composition. Accordingly, in some embodiments, the increase in feeding value of corn can be about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, and the like, and/or any range therein. In particular embodiments, the increase in the feed value of corn is about 1% to about 10% as compared to a control. In a representative embodiment, the increase in the feed value is about 5% as compared to a control.

In further aspects of the invention, the feed to gain ratio by the animal is reduced, optionally by about 0.005 to about 0.1, as compared to a control animal that is not fed the animal feed composition. The efficiency of feed utilization, also known as "F:G", is the dry matter intake per day divided by the average daily gain of the animal. Accordingly, in some embodiments, the decrease in the feed to gain ratio can be at least about 0.005, 0.006, 0.007, 0.008, 0.009, 0.01, 0.011, 0.012, 0.013, 0.014, 0.015, 0.016, 0.017, 0.018, 0.019, 0.02, 0.021, 0.022, 0.023, 0.024, 0.025, 0.026, 0.027, 0.028, 0.029, 0.03, 0.035, 0.04, 0.045, 0.05 and the like, or any range therein. In particular embodiments, the decrease in the feed to gain ratio is about 0.005, 0.01, or 0.015 to about 0.01, 0.015, 0.02, 0.025, 0.03, 0.035. 0.040, 0.045, 0.05, 0.055, 0.06, 0.065, 0.07, or 0.075, including any combination of lower and upper values as long as the lower value is less than the upper value, as compared to a control.

In further embodiments, the invention provides a method of increasing the efficiency of feed utilization for milk production by a dairy animal, the method comprising feeding to the animal, in an amount effective to increase the efficiency of feed utilization by the dairy animal, an animal feed composition of the invention. The efficiency of feed utilization can be calculated as the amount (pounds) of milk produced per head per day divided by the amount of feed consumed on a dry matter basis. In embodiments, the efficiency of milk production is increased by at least about 0.01, 0.02, 0.03, 0.04, 0.05, 0.06, 0.07, 0.08, 0.09 or 0.1. In further embodiments, the efficiency of milk production is increased by about 0.01 to about 0.01, 0125, 0.015 or 0.2; by about 0.02 to about 0.01, 0.0125, 0.015 or 0.2; by about 0.03 to about 0.01, 0.0125, 0.015 or 0.2; by about 0.04 to about 0.01, 0.0125, 0.015 or 0.2; or by about 0.05 to about 0.01, 0.0125, 0.015 or 0.2.

In some embodiments, the animal is fed about 1 lb to about 30 lbs of an animal feed composition of the invention per animal per day. Accordingly, in some embodiments, the animal is fed about 1 lb, 2 lbs, 3 lbs, 4 lbs, 5 lbs, 6 lbs, 7 lbs, 8 lbs, 9 lbs, 10 lbs, 11 lbs, 12 lbs, 13 lbs, 14 lbs, 15 lbs, 16 lbs, 17 lbs, 18 lbs, 19 lbs, 20 lbs, 21 lbs, 22 lbs, 23 lbs, 24 lbs, 25 lbs, 26 lbs, 27 lbs, 28 lbs, 29 lbs, 30 lbs of the animal feed composition of the invention per animal per day, and the like, and/or any range therein. In some embodiments, the animal is fed about 9 lbs to about 21 lbs of the animal feed composition of the invention per animal per day. In some embodiments, an animal can be fed the animal feed composition of the invention ad libitum, or about one time to about three times per day (e.g., 1, 2, 3) or any combination thereof. The animal feed composition of the present invention can be fed to any animal, for example, a farm animal, a zoo animal, a laboratory animal and/or a companion animal. In embodiments, the animal is a ruminant animal. In some embodiments, the animal can be, but is not limited to, a bovine (e.g., domestic cattle including *Bos taurus* and/or *B. indicus*, [e.g., dairy and/or beef cattle], bison, buffalo), an equine (e.g., horse, donkey, zebra, and the like), an avian (e.g., a chicken, a quail, a turkey, a duck, and the like; e.g., poultry), a sheep, a goat, an antelope, a pig (e.g., swine), a canine, a feline, a rodent (e.g., mouse, rat, guinea pig); a rabbit, a fish, and the like. Domestic cattle include calves, steers, heifers and/or cows. In embodiments, a domesticated bovine being raised for beef is a steer and/or a heifer (e.g., on a feeding lot). In embodiments, a domesticated bovine being raised for beef is a growing calf after weaning (e.g., a backgrounder or stocker beef calf), optionally being raised to go to a feedlot for finishing. Domestic dairy animals include cows and/or goats. In some embodiments the animal can be poultry. In other embodiments, the animal can be a chicken. In further embodiments, the animal can be swine. In still further embodiments, the animal can be a pig.

According to the methods of the invention to increase the weight gain and/or efficiency of feed utilization of an animal being raised for meat production, the animal can be fed an animal feed composition of the invention for any suitable time to achieve the desired outcome. In embodiments, the animal is fed a composition of the invention for at least about 15, 30, 45, 60 or 90 days to about 30, 60, 90, 120, 150, 180, 240, or 300 days, and any range therein as long as the lower value is less than the upper value. In some embodiments, the animal is fed an animal feed of the invention for a period of about 30 days to about 275 days, about 45 days to about 250 days, about 60 days to about 225 days, about 75 days to about 200 days, about 100 days to about 275 days, about 125 days to about 250 days, about 150 days to about 225 days, about 180 days to about 200 days, and the like.

Accordingly, in some embodiments, the animal is fed an animal feed composition of the invention for at least about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300 or more days, and the like, and/or any range therein.

In the case of beef cattle, the animal can be fed the animal feed composition during the backgrounding and/or finishing (feedlot) stage.

In further embodiments, the present invention provides a method for increasing the amount (e.g., measured as volume or weight) of milk produced by a dairy animal (e.g., a cow, a goat, and the like), comprising feeding to the dairy animal an animal feed composition of the present invention. In embodiments, the amount of milk produced by the animal is increased by about 1, 2, 3, 4, or 5% to about 10, 15, 20, 25, 50, 75, 100, 125, 150 or 200% (including ranges encompassed by any combination of lower value and upper value) as compared to the amount of milk produced by a control animal that is not provided the animal feed composition of the invention. In other embodiments, the amount of milk produced by the animal is increased by about 1% to about 50%, about 2% to about 50%, about 1% to about 25%, about 2% to about 25%, about 1% to about 15%, about 2% to about 15%, about 1% to about 10%, about 2% to about 10%, and the like. In further embodiments, the amount of milk produced by the animal is increased by at least about 1%, 2% 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195% and/or 200% as compared to a control animal that has not been fed the animal feed composition of the invention. The increase in milk production can be measured over any suitable time period, e.g., on a daily basis (e.g., 24 hours), about 48 hours, about 72 hours, weekly, monthly, or even total milk production over the entire lactation cycle.

According to the methods of the invention to increase milk production and/or efficiency of feed utilization of a dairy animal, the animal can be fed an animal feed composition of the invention for any suitable time to achieve the desired outcome. In embodiments, the animal is fed a composition of the invention for at least about 15, 30, 45, 60 or 90 days to about 30, 60, 90, 120, 150, 180, 240, or 300 days, and any range therein as long as the lower value is less than the upper value. In some embodiments, the animal is fed an animal feed of the invention for a period of about 30 days to about 275 days, about 45 days to about 250 days, about 60 days to about 225 days, about 75 days to about 200 days, and the like.

Accordingly, in some embodiments, the dairy animal is fed an animal feed composition of the invention for at least about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300 or more days, and the like, and/or any range therein.

Further, dairy animals can be fed the animal feed composition during the dry period (e.g., during gestation, optionally, at least the last 2, 3, 4, 6 or 8 weeks of gestation) and/or during the lactation period.

The invention also contemplates methods of treating, preventing and/or reducing the onset, duration and/or severity of a microbial or fungal infection in an animal. In embodiments, the animal is a ruminant animal (e.g., a bovine animal subject, as described above, including beef cattle and dairy cows). In embodiments, the infection is an infection with a bacterial, yeast and/or protozoan organism. In embodiments, the infection is an infection of the gut (e.g., the hind gut). In embodiments, the infection is an infection with a species of *Clostridium*, e.g., *C. perfringens*, optionally *C. perfringens* Type A. Without being limited by any theory of the invention, it is known in the art that undigested starch in the gut, particularly the hind gut, can result in microbial infection. The improved digestibility of starch in the animal feeds of the present invention may therefore be advantageous to treat, prevent and/or reduce the onset, duration and/or severity or microbial infections.

The terms "increase," "increasing," "increased," "enhance," "enhanced," "enhancing," and "enhancement" (and grammatical variations thereof), as used herein, describe an increase in the specified parameter by feeding to an animal an animal feed composition of the invention, wherein the specified parameter is elevated as compared with an animal not fed an animal feed composition of the invention (i.e., a control), for example is fed a conventional feed that does not comprise the exogenous alpha amylase.

As used herein, the terms "reduce," "reduced," "reducing," "reduction," "diminish," "suppress," and "decrease" (and grammatical variations thereof), describe, for example, a reduction of or decrease in the specified parameter by feeding to an animal an animal feed composition of the invention, wherein the specified parameter is lower as compared with a suitable control animal (e.g., a control animal that is not fed the animal feed composition comprising the exogenous alpha amylase).

The present invention is more particularly described in the following examples that are intended as illustrative only since numerous modifications and variations therein will be apparent to those skilled in the art.

Example 1

Beef Cattle Finishing Studies

Experiment 1

Three hundred crossbred steers (Initial BW=658±36 lbs) were utilized in a feedlot finishing trial at the UNL Agricultural Research and Development Center (ARDC) feedlot near Mead, Nebr. Cattle were limit fed a diet at 2% BW consisting of 32% corn wet distillers grains plus solubles, 32% alfalfa hay, 32% dry-rolled corn, and 4% supplement (DM basis) for five d prior to the start of the experiment. Two-day initial weights were recorded on d 0 and 1 which were averaged and used as the initial BW. The steers were blocked by BW into light, medium, and heavy BW blocks (n=3, 2, and 1 pen replicates, respectively), stratified by BW and assigned randomly to one of 30 pens with pens assigned randomly to one of five dietary treatments. There were 10 head/pen and 6 replications/treatment. Dietary treatments included 1) commercial corn source (CON), 2) Enogen® test corn (SYN), 3) 50:50 blend of CON and SYN, 4) CON with wet corn gluten feed (CON-SB), and 5) SYN with wet corn gluten feed (SYN-SB) in a randomized block design (Table 1). Steers were adapted to the finishing diets over a 21-d period with corn replacing alfalfa hay, while inclusion of corn silage, corn wet distillers grain plus solubles (WDGS), and supplement remained the same in all diets. In diets containing wet corn gluten feed (Sweet Bran® (Cargill); SB) the concentration remained the same in all grain adaptation diets. Diets were formulated to meet or exceed NRC requirements for protein and minerals. The final finishing diets provided 360 mg/steer daily of Rumensin® (30 g/ton of DM), and 90 mg/steer daily of Tylan® (9 g/ton of DM). Steers were implanted on d 1 with Revalor®-XS.

All steers were harvested at a commercial abattoir (Greater Omaha Pack, Omaha, Neb.) on d 173. Final live BW was collected on the d of slaughter and a 4% pencil shrink was applied for calculation of dressing percentage. Feed offered on d 173 was 50% of the previous day DMI and weighed at 4:00 pm. Steers were then shipped and held until slaughter the next day. Hot carcass weight and livers scores were recorded on the d of slaughter. Fat thickness, LM area, and USDA marbling score were recorded after a 48-h chill. Final BW, ADG, and F:G were calculated using HCW adjusted to a common 63% dressing percentage.

Experiment 2

Two hundred-forty crossbred steers (Initial BW=634±34 lbs) were utilized in a feedlot finishing trial at the UNL Panhandle Research and Extension Center (PHREC) feedlot near Scottsbluff, Neb. Cattle limit feeding and initial BW protocols were the same as Exp 1. The steers were blocked by BW into light, medium, and heavy BW blocks, stratified by BW and assigned randomly to one of 24 pens with pens assigned randomly to one of four dietary treatments. There were 10 head per pen and 6 replications per treatment. Dietary treatments included 1) CON, 2) SYN, 3) BLEND, and 4) CON with enzyme (Amaize; Alltech, Inc.) added to the diet at a rate of 5 g/steer daily (NZ; Table 2). Limit feeding, weighing, blocking, implanting, and grain adaptation procedures were the same as Exp 1. Steers in the heavy, middle, and light BW blocks were harvested at a commercial abattoir (Cargill Meat Solutions, Fort Morgan, Colo.) on days 148, 169 and 181 (respectively). On the final day steers were withheld from feed and weighed at 8:00 am before being shipped and slaughtered on the same day. Data were analyzed as a randomized block design with initial BW block as a fixed effect and pen as the experimental unit.

TABLE 1

Dietary treatments evaluating test corn and conventional corn with or without Sweet Bran (Exp 1).

| Ingredient, % DM | CON | SYN | BLEND | CON-CGF[1] | SYN-CGF[2] |
|---|---|---|---|---|---|
| Commercial Corn | 68.0 | — | 34.0 | 58.0 | — |
| Test corn[3] | — | 68.0 | 34.0 | — | 58.0 |
| Sweet Bran | — | — | — | 25.0 | 25.0 |
| MDGS[4] | 15.0 | 15.0 | 15.0 | — | — |

TABLE 1-continued

Dietary treatments evaluating test corn and conventional corn with or without Sweet Bran (Exp 1).

| Ingredient, % DM | CON | SYN | BLEND | CON-CGF[1] | SYN-CGF[2] |
|---|---|---|---|---|---|
| Corn silage | 12.0 | 12.0 | 12.0 | 12.0 | 12.0 |
| Meal supplement[5] | 5.0 | 5.0 | 5.0 | 5.0 | 5.0 |
| Fine ground corn | 2.174 | 2.174 | 2.174 | 2.435 | 2.435 |
| Limestone | 1.6 | 1.6 | 1.6 | 1.6 | 1.6 |
| Urea | 0.6 | 0.6 | 0.6 | 0.4 | 0.4 |
| Salt | 0.3 | 0.3 | 0.3 | 0.3 | 0.3 |
| Tallow | 0.125 | 0.125 | 0.125 | 0.125 | 0.125 |
| Trace mineral premix | 0.05 | 0.05 | 0.05 | 0.05 | 0.05 |
| Potassium chloride | 0.02 | 0.02 | 0.02 | — | — |
| Rumensin-90 | 0.0165 | 0.0165 | 0.0165 | 0.0165 | 0.0165 |
| Vitamin ADE premix | 0.015 | 0.015 | 0.015 | 0.015 | 0.015 |
| Tylan-40 | 0.01 | 0.01 | 0.01 | 0.01 | 0.01 |
| Analyzed Nutrient Composition, % | | | | | |
| Starch | 52.48 | 52.55 | 52.52 | 47.75 | 47.81 |
| CP | 12.84 | 12.91 | 12.88 | 12.58 | 12.64 |
| Fat | 4.07 | 4.01 | 4.04 | 3.19 | 3.13 |
| NDF | 15.91 | 15.16 | 15.54 | 18.80 | 18.16 |
| S | 0.16 | 0.15 | 0.15 | 0.19 | 0.18 |
| P | 0.40 | 0.39 | 0.39 | 0.46 | 0.44 |
| K | 0.57 | 0.58 | 0.57 | 0.67 | 0.68 |
| Mg | 0.17 | 0.17 | 0.17 | 0.19 | 0.19 |

[1]Conventional corn with wet corn gluten feed, Sweet Bran
[2]Syngenta test corn with wet corn gluten feed, Sweet Bran
[3]Test corn provided by Syngenta under identity-preserved procedures. Stored, processed, and fed separately
[4]MDGS = modified distillers grains with solubles
[5]Supplement included 30 g/ton Rumensin ® and 9 g/ton Tylan ®.

TABLE 2

Dietary treatments evaluating test corn and conventional corn with or without added enzyme (Exp 2).

| Ingredient | CON | SYN | BLEND | CON-NZ |
|---|---|---|---|---|
| Corn | 64.0 | — | 32.0 | 64.0 |
| Test corn | — | 64.0 | 32.0 | — |
| WDGS | 15.0 | 15.0 | 15.0 | 15.0 |
| Corn silage | 15.0 | 15.0 | 15.0 | 15.0 |
| Liquid Supplement[2,3] | 6.0 | 6.0 | 6.0 | 6.0[4] |
| Analyzed Nutrient Composition, % | | | | |
| Starch | 51.40 | 52.23 | 51.82 | 51.40 |
| CP | 12.96 | 13.41 | 13.18 | 12.96 |
| Fat | 3.44 | 3.89 | 3.67 | 3.44 |
| NDF | 15.46 | 15.66 | 15.56 | 15.46 |
| S | 0.15 | 0.15 | 0.15 | 0.15 |
| P | 0.34 | 0.31 | 0.32 | 0.34 |
| K | 0.54 | 0.52 | 0.53 | 0.54 |
| Mg | 0.15 | 0.15 | 0.15 | 0.15 |

[2]Liquid supplement contained; 0.6% urea, 1.6% Ca, 0.3% salt, 0.02% potassium chloride, vitamins and trace minerals.
[3]Rumensin ® (30 g/ton) and Tylan ® (9 g/ton) were added via micromachine.
[4]Enzyme added via micro-machine at the rate of 5 g/steer daily

TABLE 3

Effect of corn hybrid on finishing steer performance and carcass characteristics without Sweet Bran (Exp. 1)

| | Dietary Treatments[1] | | |
|---|---|---|---|
| Item | CON | SYN | BLEND |
| Animal Performance | | | |
| Initial BW, lbs | 672 | 673 | 673 |
| DMI, lbs | 23.0 | 22.4 | 23.0 |
| Final BW, lbs[4] | 1296 | 1291 | 1304 |

TABLE 3-continued

Effect of corn hybrid on finishing steer performance and carcass characteristics without Sweet Bran (Exp. 1)

| | Dietary Treatments[1] | | |
|---|---|---|---|
| Item | CON | SYN | BLEND |
| ADG, lbs[4] | 3.61 | 3.57 | 3.64 |
| G:F, lb/lb[4] | 0.159 | 0.161 | 0.159 |
| F:G, lb/lb[4,5] | 6.44 | 6.31 | 6.34 |
| Carcass Characteristics | | | |
| HCW, lbs | 816 | 814 | 821 |
| Dressing % | 62.7 | 62.8 | 62.9 |
| Marbling Score[6] | 461 | 489 | 511 |
| Fat Depth, in | 0.48[a] | 0.55[b] | 0.57[b] |
| LM Area, $in^2$ | 12.9 | 12.5 | 12.3 |
| Calculated Yield Grade[7] | 3.68[a] | 3.99[b] | 4.10[b] |
| Liver Abscesses, % | 8.33 | 5.00 | 5.37 |

[1]CON = control commercial corn hybrid, SYN = Syngenta test corn hybrid, BLEND = 50:50 blend of CON and SYN on a DM basis.
[4]Calculated from HCW adjusted to a common 63% pressing percentage.
[5]Analyzed as G:F, the reciprocal of F:G.
[6]Marbling Score: 300 = $Slight^{00}$, 400 = $Small^{00}$.
[7]Calculated as 2.5 + (2.5 × $12^{th}$ rib fat) + (0.2 × 2.5[KPH]) + (0.0038 × HCW) − ( 0.32 × LM area).
[a,b]Means within a row with unlike superscripts differ ($P < 0.05$).

TABLE 4

Effect of corn hybrid and inclusion of Sweet Bran on finishing steers performance and carcass characteristics (Exp 1)

| | Dietary Treatments[1] | | | |
|---|---|---|---|---|
| | 0% SB | | 25% SB | |
| | CON | SYN | CON | SYN |
| Animal Performance | | | | |
| Initial BW, lbs | 671 | 673 | 673 | 674 |
| DMI, lbs | 23.0 | 22.4 | 23.3 | 22.7 |
| Final BW, lbs[3] | 1295 | 1290 | 1278 | 1317 |
| ADG, lbs[3] | 3.60[ab] | 3.57[ab] | 3.49[b] | 3.72[a] |
| G:F[3] | 0.159[bc] | 0.160[ab] | 0.151[c] | 0.164[a] |
| F:G, lb/lb[4,5] | 6.44 | 6.31 | 6.71 | 6.13 |
| Carcass Characteristics | | | | |
| HCW, lbs | 816 | 813 | 805 | 829 |
| Dressing % | 62.7 | 62.8 | 62.8 | 63.1 |
| Marbling Score[5] | 456 | 484 | 443 | 488 |
| Fat Depth, in | 0.48 | 0.56 | 0.48 | 0.53 |
| Ribeye Area, $in^2$ | 12.9 | 12.5 | 12.8 | 13.0 |
| Calculated Yield Grade[6] | 3.67 | 3.98 | 3.67 | 3.83 |
| Liver Abscesses, % | 8.96 | 5.63 | 11.12 | 5.63 |

[1]0% SB =diets without Sweet Bran, 25% SB = diets containing 25% Sweet Bran, CON = commercial corn hybrid, SYN = Syngenta test corn.
[3]Calculated from HCW adjusted to a common 63% dressing percentage.
[4]Analyzed as G:F, the reciprocal of F:G.
[5]Marbling Score: 300 = Slight[00], 400 = Small[00].
[6]Calculated as 2.5 + (2.5 × $12^{th}$ rib fat) + (0.2 × 2.5[KPH]) + (0.0038 × HCW) − (0.32 × LM area).
[a,b,c]Means within a row with unlike superscripts differ ($P < 0.05$).

TABLE 5

Effect of corn hybrid and inclusion of an alpha amylase enzyme on finishing steer performance and carcass characteristics (Exp 2)

| | Dietary Treatment[1] | | | |
|---|---|---|---|---|
| Item | CON | SYN | BLEND | NZ |
| Animal Performance | | | | |
| Initial BW, lbs | 646 | 649 | 647 | 647 |
| DMI, lbs | 23.6 | 23.8 | 23.5 | 23.4 |
| Final BW, lbs[3] | 1257[a] | 1301[b] | 1299[b] | 1299[b] |
| ADG, lbs[3] | 3.71[a] | 3.94[b] | 3.93[b] | 3.93[b] |
| G:F[3] | 0.158 | 0.165 | 0.166 | 0.167 |
| F:G, lb/lb[3,4] | 6.53 | 6.18 | 6.07 | 6.07 |
| Carcass Characteristics | | | | |
| HCW, lbs | 792[a] | 820[b] | 818[b] | 818[b] |
| Dressing % | 62.7 | 63.2 | 63.3 | 63.2 |
| Marbling Score[5] | 451[a] | 468[ab] | 481[b] | 468[ab] |
| Fat Depth, in | 0.57[a] | 0.60[ab] | 0.61[b] | 0.60[ab] |
| Ribeye Area, $in^2$ | 12.1[a] | 12.1[a] | 12.4[b] | 12.4[b] |
| Calculated Yield Grade[6] | 3.47 | 3.64 | 3.55 | 3.55 |
| Liver Abscesses, % | 3.33 | 5.00 | 0 | 5.33 |

[1]CON = commercial corn hybrid, SYN = Syngenta test corn, BLEND = 50:50 blend of CON and SYN on a DM basis, NZ = inclusion of a commercially available alpha amylase enzyme in diets based on CON.
[23]Calculated from HCW adjusted to a common 63% pressing percentage.
[4]Analyzed as G:F, the reciprocal of F:G.
[5]Marbling Score: 300 = Slight[00], 400 = Small[00].
[6]Calculated as 2.5 + (2.5 × $12^{th}$ rib fat) + (0.2 × 2.5[KPH]) + (0.0038 × HCW) − (0.32 × LM area).
[a,b]Means within a row with unlike superscripts differ ($P < 0.05$).

Experiment 3

A 173-d finishing trial was conducted utilizing a number of crossbred steers (initial BW (Body Weight)=685±46 lbs) in a randomized block design. Steers were limit fed a diet at 2% BW consisting of 47.5% alfalfa hay, 47.5% wet corn gluten feed, and 5% supplement (DM (Dry Matter) basis) for five d prior to the initiation of the experiment. Two-day initial weights were recorded on d 0 and 1 and averaged to determine initial BW. Along with measuring initial BW on d 1, steers were implanted with Revalor®-XS. The steers were blocked by BW into light and heavy BW blocks stratified by BW and assigned randomly to pen. Pens were then assigned randomly to a dietary treatment with 8 head/pen and 6 replications/treatment.

Dietary treatments (Table 6) were arranged with factors including test corn or control (Enogen® or Non-Enogen®), and byproduct type (MDGS (Modified Distillers Grains with Solubles) or Sweet Bran). The byproducts utilized in this trial were provided as either a protein source (18% MDGS) or as a means of acidosis control (35% SB (Sweet Bran® (Cargill))). Steers were adapted to the finishing diets over a 21-d period with corn replacing alfalfa hay, while inclusion of sorghum silage, Sweet Bran or MDGS, and supplement remained the same in all diets. Diets were formulated to meet or exceed NRC requirements for protein and minerals. The final finishing diets provided 330 mg/steer daily of Rumensin® (30 g/ton of DM), and 90 mg/steer daily of Tylan® (8.18 g/ton of DM).

All steers were harvested on d 174 at a commercial abattoir (Greater Omaha Pack, Omaha, Nebr.). Feed offered on d 173 was 50% of the previous day DMI and weighed at 4:00 pm. Steers were then shipped to the commercial abattoir and held until the next day for slaughter. Hot carcass weights and livers scores were recorded on the d of slaughter with carcass characteristics such as 12th rib fat thickness, LM area, and USDA marbling score being recorded after a 48-h chill. Yield grade was calculated using the USDA YG equation [YG=2.5+2.5 (fat thickness, in)−0.32 (LM area, $in^2$)+0.2 (KPH fat, %)+0.0038 (HCW, lb)]. Final BW, ADG (Average Daily Gain), and G:F (Gain to Feed ratio) were calculated using HCW (Hot Carcass Weight) adjusted to a common 63% dressing percentage.

TABLE 6

Diet Composition on a DM basis fed to finishing steers

| Ingredient, % DM | Test Corn | | | | Control | | | |
|---|---|---|---|---|---|---|---|---|
| | MDGS[1] | | Sweet Bran | | MDGS[1] | | Sweet Bran | |
| Test Corn DRC[2] | 69.5 | — | 52.5 | | — | — | — | |
| Control DRC[2] | — | — | — | — | 69.5 | — | 52.5 | — |
| Sweet Bran | — | — | 35.0 | 35.0 | — | — | 35.0 | 35.0 |
| Modified distillers grains plus solubles | 18.0 | 18.0 | — | — | 18.0 | 18.0 | — | — |
| Sorghum Silage | 7.5 | 7.5 | 7.5 | 7.5 | 7.5 | 7.5 | 7.5 | 7.5 |
| Meal Supplement[4] | 5.0 | 5.0 | 5.0 | 5.0 | 5.0 | 5.0 | 5.0 | 5.0 |
| Fine ground corn | 2.223 | 2.223 | 2.806 | 2.806 | 2.223 | 2.223 | 2.806 | 2.806 |
| Limestone | 1.71 | 1.71 | 1.68 | 1.68 | 1.71 | 1.71 | 1.68 | 1.68 |
| Urea | 0.55 | 0.55 | — | — | 0.55 | 0.55 | — | — |
| Salt | 0.3 | 0.3 | 0.3 | 0.3 | 0.3 | 0.3 | 0.3 | 0.3 |
| Tallow | 0.125 | 0.125 | 0.125 | 0.125 | 0.125 | 0.125 | 0.125 | 0.125 |
| Trace mineral premix | 0.05 | 0.05 | 0.05 | 0.05 | 0.05 | 0.05 | 0.05 | 0.05 |
| Rumensin-90 | 0.0165 | 0.0165 | 0.0165 | 0.0165 | 0.0165 | 0.0165 | 0.0165 | 0.0165 |
| Vitamin ADE premix | 0.015 | 0.015 | 0.015 | 0.015 | 0.015 | 0.015 | 0.015 | 0.015 |
| Tylan-40 | 0.01 | 0.01 | 0.01 | 0.01 | 0.01 | 0.01 | 0.01 | 0.01 |
| Analyzed Nutrient Composition, % | | | | | | | | |
| Starch | 47.56 | 49.08 | 39.06 | 40.21 | 47.14 | 48.74 | 38.74 | 39.95 |
| CP | 12.1 | 12.0 | 13.5 | 13.4 | 12.2 | 12.0 | 13.6 | 13.4 |
| Fat | 4.35 | 4.98 | 3.19 | 3.66 | 4.35 | 5.19 | 3.19 | 3.82 |
| NDF | 15.5 | 14.9 | 20.0 | 19.5 | 16.2 | 15.4 | 20.5 | 19.9 |
| S | 0.22 | 0.22 | 0.21 | 0.16 | 0.22 | 0.21 | 0.21 | 0.21 |
| P | 0.38 | 0.39 | 0.53 | 0.53 | 0.34 | 0.35 | 0.50 | 0.51 |
| K | 0.47 | 0.48 | 0.68 | 0.68 | 0.45 | 0.45 | 0.66 | 0.66 |
| Mg | 0.17 | 0.17 | 0.24 | 0.24 | 0.16 | 0.16 | 0.23 | 0.23 |

[1]MDGS = Modified distillers grains plus solubles
[2]DRC = Dry rolled corn
[4]Supplement included 30 g/ton Rumensin ® and 9 g/ton Tylan ®

TABLE 7

Effects of test corn on finishing cattle performance

| | DRC[1] | |
|---|---|---|
| | Test Corn | Control |
| Performance | | |
| Initial BW, lb | 700 | 699 |
| Final BW, lb[5] | 1451[b] | 1433[a] |
| DMI, lb/d | 23.7 | 23.8 |
| ADG, lb[5] | 4.36[b] | 4.25[ab] |
| G:F[5] | 0.184 | 0.178 |
| Carcass Characteristics | | |
| HCW, lb | 912 | 904 |
| Marbling[6] | 505 | 492 |
| LM area, in[2] | 14.3 | 14.0 |
| Fat Depth, in | 0.55 | 0.59 |
| Cal. YG[7] | 3.24 | 3.41 |

[1]DRC = Dry rolled corn;
[5]Calculated from HCW adjusted to a common 63% dressing percentage
[6]Marbling Score: 400 = Small00; 500 = Modest00
[7]Calculated as 2.5 + (2.5 × 12th rib fat) + (0.2 × 2.5[KPH]) + (0.0038 × HCW) − (0.32 × LM area)
[a,b]Means within a row with unlike superscripts differ ($P < 0.10$).

TABLE 8

Effects of test corn and byproduct type on finishing cattle performance

| | MDGS[1] | | Sweet Bran | |
|---|---|---|---|---|
| | Test Corn | Control | Test Corn | Control |
| Performance | | | | |
| Initial BW, lb | 700 | 698 | 699 | 700 |
| Final BW, lb[5] | 1434 | 1427 | 1447 | 1453 |
| DMI, lb/d | 22.5 | 22.9 | 23.3 | 23.4 |
| ADG, lb[5] | 4.25 | 4.21 | 4.34 | 4.36 |
| G:F[5] | 0.190 | 0.184 | 0.186 | 0.187 |
| Carcass Characteristics | | | | |
| HCW, lb | 903 | 899 | 913 | 916 |
| Marbling[6] | 488 | 494 | 510 | 506 |
| LM area, in[2] | 14.4 | 14.0 | 14.1 | 14.1 |
| Fat Depth, in | 0.56 | 0.59 | 0.59 | 0.58 |
| Cal. YG[7] | 3.21 | 3.43 | 3.42 | 3.40 |

[1]MDGS = Modified distillers grains plus solubles
[5]Calculated from HCW adjusted to a common 63% dressing percentage
[6]Marbling Score: 400 = Small[00]; 500 = Modest[00]
[7]Calculated as 2.5 + (2.5 × 12th rib fat) + (0.2 × 2.5[KPH]) + (0.0038 × HCW) − (0.32 × LM area)

Example 2

Additional Finishing Studies with Enogen® Feed Corn

Two finishing experiments were conducted to evaluate Enogen® Feed corn (EFC) containing an alpha amylase enzyme trait compared to the near negative isoline control corn at two locations on cattle performance and carcass characteristics.

Experimental:

Three-hundred crossbred steers (initial body weight [BW] =703 lb, ±43) were utilized in a finishing trial at the University of Nebraska-Lincoln (UNL) Eastern Nebraska Research and Extension Center (ENREC) feedlot near Mead, Neb., All corn (EFC and near negative isoline parental control corn [NEG] seed from Syngenta Seeds, LLC) was grown during the summer at ENREC, harvested in November, and processed as dry rolled corn (DRC) at time of feeding. Cattle were limit fed a diet at 2% of BW for 5 days prior to the start of the experiment. Two-day initial weights were recorded on days 0 and 1, which were averaged and used as the initial BW.

The steers were blocked by BW into two weight blocks, light and heavy, (n=10 and 5 pen replicates, respectively) based on day 0 BW, stratified by BW within block and assigned randomly to 1 of 30 pens. Pen was assigned randomly to treatment. There were 10 steers/pen and 15 replications/treatment.

Dietary treatments included 1) EFC and 2) Near negative isoline parental control (NEG; Table 9). Steers were adapted to the finishing diets over a 21-day period with corn replacing alfalfa hay, while inclusion of corn silage, modified distillers grain plus solubles (MDGS), and supplement remained the same in all diets. Diets were formulated to meet or exceed NRC requirements for protein and minerals. The final finishing diets provided 330 mg/steer daily of Rumensin® (30 g/ton of dry matter [DM]; Elanco Animal Health, Greenfield, Ind.), and 90 mg/steer daily of Tylan® (8.2 g/ton of DM; Elanco Animal Health, Greenfield, Ind.). Steers were implanted with Component® IS (Elanco Animal Health, Greenfield, Ind.) on day 22 and Component® S (Elanco Animal Health, Greenfield, Ind.) on day 92.

On day 169, feed was offered at 50% of the previous day dry matter intake (DMI), and cattle were weighed at 1500 h to determine final live BW. A 4% pencil shrink was applied to the final live BW to calculate dressing percentage. All steers were harvested at a commercial abattoir (Greater Omaha, Omaha, Neb.) on day 170 and hot carcass weights (HCW) and liver scores were recorded on the day of slaughter. Fat thickness, longissimus muscle (LM) area, and USDA marbling score were recorded after a 48-hour chill period. Yield grade (YG) was calculated using the USDA YG equation [YG=2.5+2.5 (fat thickness, in)−0.32 (LM area, $in^2$)+0.2 (kidney pelvic and heart [KPH] fat, %)+0.0038 (HCW, lb)]. Final BW, average daily gain (ADG), and feed:gain (F:G) were calculated using HCW adjusted to a common 63% dressing percentage.

In a second study, three-hundred crossbred steers (initial BW=624 lb, ±34) were utilized in a finishing trial at the UNL Panhandle Research and Extension Center (PREC) feedlot near Scottsbluff, Neb. All corn utilized was grown at the ENREC and shipped to the PREC during the trial. Initial BW protocols, BW blocking, treatment assignment, number of steers per pen, and replications per treatment were the same as described above at ENREC. Steers were adapted to the finishing diets over a 21-day period with corn replacing alfalfa hay, while inclusion of corn silage, wet distillers grain plus solubles (WDGS), and supplement remained the same in all diets. Dietary treatments were the same as ENREC with the exception of WDGS in place of MDGS and the inclusion of supplement at 6% instead of 4% of the diet DM. Steers were implanted with Component® IS (Elanco Animal Health, Greenfield, Ind.) on day 1 and Component® S (Elanco Animal Health, Greenfield, Ind.) on day 91. Steers were harvested at a commercial abattoir (Cargill Meat Solutions, Fort Morgan, Colo.) on day 181. Carcass data collection procedures and calculations were the same as described above.

Overall, 600 steers were utilized between the two locations to provide a total of 30 replications per treatment. Performance and carcass characteristic data were analyzed using the MIXED procedure of SAS (Cary, N.C.) as a generalized randomized block design with pen as the experimental unit. Liver abscess incidence data were analyzed using the GLIMMIX procedure of SAS (Cary, N.C.) with the number of animals affected by liver abscesses divided by the total number of animals within the pen as binomial variables. The effect of location, treatment, and location×treatment were all included in the model with BW block as a fixed variable. If the location×treatment interaction was not significant (P≥0.05), main effects were discussed and the interaction term was removed from the model.

Results:

There were no treatment by location interactions (P≥0.30) observed for initial BW, final BW, DMI, ADG, F:G, and liver abscess percentage (data not shown). No significant differences in final BW, DMI, ADG, F:G, or liver abscess percentage were observed for steers fed EFC compared to NEG (P≥0.17; Table 10). A small (2% due to grain) numerical decrease (P=0.17) in F:G was observed for steers fed EFC as compared to NEG. A location effect (P≤0.03) was observed for final BW, DMI, ADG, and F:G with steers fed at PREC having greater final BW, DMI, ADG, and decreased F:G compared to ENREC (data not shown). Previous research has shown positive results in cattle performance with steers fed EFC processed as DRC. Overall, greater ADG and improvements in F:G have been reported in steers fed EFC compared to commercial corn or NEG (2016 *Nebraska Beef Report pp.* 135; 2016 *Nebraska Beef Report* pp. 143).

Fat depth and calculated YG were greater (P<0.01 and P=0.02, respectively) for steers fed EFC compared to NEG; however LM area was slightly greater (P=0.02) for NEG. Previous research has reported either an increase in fat depth (P≤0.03) and calculated YG (P≤0.03; 2016 *Nebraska Beef Report pp.* 135) or no difference (P≤0.22 and P≤0.17, respectively; 2016 *Nebraska Beef Report pp.* 135; 2016 *Nebraska Beef Report* pp. 143) when steers were fed EFC.

No significant differences by treatment were observed for HCW or marbling score (P≥0.33). Previous research has reported mixed results for marbling score of steers fed SYT-EFC compared to commercial corn or NEG either observing an increase (2016 *Nebraska Beef Report* pp. 135) or no difference (2016 *Nebraska Beef Report* pp. 143).

Differences in cattle response between previous trials and this current trial could be attributed to growing conditions of the corn resulting in a year effect.

In conclusion, previous finishing trials have observed a decrease in F:G when EFC has been fed as the main source of dietary corn grain. However, results from this trial would suggest that there is no significant change in F:G by feeding the Syngenta Enogen Feed Corn hybrid containing an alpha amylase enzyme trait as the response was too small to detect. The change in F:G was only 1% due to diet, which is assumed to be only 1.6% due to corn grain (65% of the diet, average between ENREC and PREC).

TABLE 9

| Dietary treatments evaluating Enogen ® Feed Corn and Near Negative Isoline Parental Control Corn | | |
|---|---|---|
| Ingredient, % DM | NEG[1] | SYT-EFC[2] |
| NEG[1] | 66.0 | — |
| SYT-EFC[2] | — | 66.0 |
| DGS[3] | 18.0 | 18.0 |
| Corn silage | 12.0 | 12.0 |
| Meal supplement (ENREC)[4] | 4.0 | 4.0 |
| Fine ground corn | 1.2362 | 1.2362 |
| Limestone | 1.689 | 1.689 |
| Urea | 0.5 | 0.5 |
| Salt | 0.3 | 0.3 |
| Tallow | 0.10 | 0.10 |
| Trace mineral premix | 0.05 | 0.05 |
| Potassium chloride | 0.083 | 0.083 |
| Rumensin-90 | 0.0165 | 0.0165 |
| Vitamin ADE premix | 0.015 | 0.015 |
| Tylan-40 | 0.0102 | 0.0102 |
| Liquid Supplement (PHREC)[5,6] | 6.0 | 6.0 |

[1]NEG: Near negative isoline parental control corn
[2]SYT-EFC: Syngenta Enogen Feed Corn containing α-amylase enzyme
[3]DGS: Distillers grains plus solubles
[4]Meal Supplement fed at the Eastern Nebraska Research and Extension Center
[5]Liquid Supplement fed at the Panhandle Research and Extension Center
[6]Supplement formulated to provide a dietary DM inclusion of 1.34% limestone, 0.5% urea, 0.3% salt, 0.2% potassium chloride, 30 mg/kg Zn, 50 mg/kg Fe, 10 mg/kg Cu, 20 mg/kg Mn, 0.1 mg/kg Co, 0.5 mg/kg I, 0.1 mg/kg Se, 1000 IU of vitamin A, 125 IU of vitamin D, 1.5 IU of vitamin E.

Agricultural Research and Teaching (FASS, First Revised Edition, January 1999). All procedures outlined as part of this study are in accordance with University of Nebraska animal care protocols.

Design and Allotment

Steers are limit-fed at an estimated 2% of body weight (BW) a 50% alfalfa, 50% wet corn gluten feed (WCGF) diet for 5 days prior to weighing. Weights are collected on individuals two consecutive days to minimize gut fill effects and get an accurate initial body weight.

This study utilizes 336 steers (8 steers/pen). Steers are assigned randomly to pens based on the first day weight. Blocking criteria may be used depending on range in body weight. Pens are assigned randomly to one of 7 treatments described below. This study is designed as a completely randomized design (or randomized block design if blocking criteria are required) with 7 treatments arranged as a 2×3+1 factorial arrangement of treatments. Pen is the experimental unit, and there are 6 replications per simple effect treatment, or a total of 42 pens with 7 treatments.

Diets and Feeding

Treatment diet composition is described Table 11. The treatment structure is organized as a 2×3 factorial along with 1 additional comparison treatment. In the factorial arrangement, factors include grain with or without the alpha amylase expression trait and fed as a ratio of high-moisture corn

TABLE 10

| Effect of corn hybrid on finishing performance and carcass characteristics | | | | | |
|---|---|---|---|---|---|
| | Dietary Treatments[1] | | | P-Values | |
| Item | NEG | SYT-EFC | SEM | Trt | Location |
| Animal Performance | | | | | |
| Initial BW, lb | 669 | 668 | 0.5 | 0.13 | <0.01 |
| Final BW, lb[2] | 1351 | 1350 | 4.9 | 0.88 | 0.03 |
| DMI, lb/d | 22.8 | 22.6 | 0.13 | 0.19 | <0.01 |
| ADG, lb[2] | 3.90 | 3.90 | 0.03 | 0.99 | <0.01 |
| F:G[2,3] | 5.85 | 5.79 | — | 0.17 | <0.01 |
| Carcass Characteristics | | | | | |
| HCW, lbs | 852 | 852 | 3.1 | 0.88 | 0.03 |
| Marbling Score[4] | 470 | 486 | 12 | 0.33 | 0.34 |
| Fat Depth, in | 0.53 | 0.56 | 0.01 | <0.01 | 0.79 |
| LM Area, in[2] | 13.2 | 13.0 | 0.07 | 0.02 | 0.44 |
| Calculated Yield Grade[5] | 3.24 | 3.49 | 0.08 | 0.02 | 0.23 |
| Liver Abscess, % | 8.60 | 6.03 | 2.33 | 0.25 | 0.81 |

[1]Dietary treatments: NEG = Near negative isoline parental control corn; SYT − EFC = Syngenta Enogen Feed Corn containing alpha amylase enzyme
[2]Calculated from HCW adjusted to a common 63% pressing percentage.
[3]Analyzed as G:F, the reciprocal of F:G.
[4]Marbling Score: 300 = Slight$^{00}$, 400 = Small$^{00}$.
[5]Calculated as 2.5 + (2.5 × 12$^{th}$ rib fat) + (0.2 × 2.0 [KPH]) + (0.0038 × HCW) − (0.32 × LM area).

Example 3

Finishing Beef Cattle Study with Enogen® Feed High Moisture and Dry Rolled Corn Cattle Background All steers are received as weaned calves at the University of Nebraska Eastern Nebraska Research and Extension Center near Mead, Nebr. Calves are received for 3 to 4 weeks and graze corn residue and are backgrounded prior to the experiment to ensure all calves are healthy Animal handling and space for this experiment are in accordance to the Guide for the Care and Use of Agricultural Animals in to dry-rolled corn. An additional treatment allows for evaluation of Enogen® Feed corn (EFC) fed as dry rolled corn (DRC) with control high moisture corn (HMC).

All diets contain 20% distillers grains to provide sufficient dietary rumen undegradable protein (RUP) to meet protein requirements and align with typical inclusion of byproduct by the feed yard industry. A 5% dry meal supplement is fed with the primary components as calcium, urea for rumen degradable protein, trace mineral premix, vitamin ADE premix, and Rumensin®/Tylan® at targeted levels. The carrier for the meal supplement is finely ground corn. Diets are formulated to provide similar Ca and appropriate Ca:P ratios. The final diets provide 30 g/ton of Monensin and 8.8 g/ton of Tylan® (dry matter [DM] basis). Steers are fed once daily and diets mixed using Roto-mix feed trucks.

TABLE 11

Diets fed to growing steer calves for approximately 84 days to evaluate use of EFC as DRC, HMC or a 50:50 blend.

| | Trait: | | | | | | |
|---|---|---|---|---|---|---|---|
| Processing method: | CON[1] DRC | EFC DRC | CON HMC | EFC HMC | CON BLEND | EFC BLEND | EFC/ CON BLEND |
| Dry-rolled corn-CON | 70 | — | — | — | 35 | — | — |
| Dry-rolled corn-EFC | — | 70 | — | — | — | 35 | 35 |
| High-moisture-CON | — | — | 70 | — | 35 | — | 35 |
| High-moisture-EFC | — | — | — | 70 | — | 35 | — |
| Corn stalks (or equiv) | 5 | 5 | 5 | 5 | 5 | 5 | 5 |
| Wet distillers grains | 20 | 20 | 20 | 20 | 20 | 20 | 20 |
| Supplement[2] | 5 | 5 | 5 | 5 | 5 | 5 | 5 |

[1]CON, conventional without Enogen ® alpha-amylase trait
[2]Supplement to provide Rumensin ® ,Tylan ® ,and minerals and urea to ensure protein, mineral, and vitamin requirements are met.

Health Data

Any cattle observed to have symptoms of common ailments or disorders is treated according to Standard Operating Procedures established for the University of Nebraska. The consulting veterinarian is consulted for observed conditions that are not covered under the Animal Health Care Standard Operating Procedures. Observations of animal health are summarized in the final report.

Measurements

Cattle are weighed on two consecutive days at the beginning of the trial to establish initial body weight. Steers are implanted with conventional implant program for their size and duration of feeding. Steers are fed approximately 145 to 160 days.

Performance traits include dry matter intake, average daily gain (using limit-fed initial weight and carcass-adjusted final weight), body weight measurements including live final body weight, and carcass traits. Carcass traits that are important for collection on the day of slaughter are hot carcass weight, liver scores for abscesses, and kill order. Following a 48 hour chill, fat thickness, longissimus muscle (LM) area, marbling score, and called yield grade are measured. A calculated yield grade measure is determined assuming a 2% kidney, pelvic, heart (KPH) fat.

Example 4

Performance and Carcass Characteristics of Cattle Fed Finishing Diets Containing Enogen® Feed as Corn Grain and/or Corn Silage A study is conducted at the Kansas State University Beef Cattle Research Center with the following objectives:

1. Evaluate growth performance (daily gain, dry matter intake, and feed efficiency) of finishing cattle fed diets containing combinations of ensiled forage material and flaked grains prepared from corn hybrids with or without high amylase expression.

2. Evaluate carcass characteristics and liver abscess rates in cattle fed diets containing combinations of ensiled forage material and flaked grains prepared from corn hybrids with or without high amylase expression.

Experimental Design:

A randomized complete block design with 4 treatments and 12 replicates in a 2×2 factorialized arrangement, as follows:

Factor 1: Steam-flaked corn grain prepared from hybrids with and without high amylase expression Factor 2: Corn silage prepared from corn hybrids with and without high-amylase corn.

Pen is the experimental unit.

Study Procedures:

Test Animals: Crossbred beef cattle averaging between 750 and 900 lb initial body weight. A group of 960 study animals are selected from a population of approximately 1000 cattle.

Pretrial Processing Procedures: Prestudy processing procedures employed are typical of those used at the study site, but generally consist of body weight determination, identification with uniquely-numbered eartags, administration of vaccines and bacterins, administration of parasiticides for control of internal and external parasites, and administration of a steroidal implant. Prophylaxis with an injectable antibiotic may be used at the discretion of the clinical investigator.

Feeding and Watering: Animals nominally have ad libitum access to feed, and are fed once daily throughout the study. Bunks are monitored daily to facilitate feed management such that cattle are nominally allowed ad libitum access to diets, but with a minimum of unconsumed feed remaining in the bunks the following day. Municipal water is available throughout the study from in-pen automatic waterers that are shared between adjacent pens.

Diet Composition: Pre-trial basal diets consist of a mixture of hay, corn silage, steam-flaked corn, and supplement to provide approximately equal proportions of concentrate and roughage. Corn silage consists of non-Enogen® Feed corn (EFC) forage material.

During the trial phase, the forage component of the diet consists entirely of corn silage. Beginning on day 1 of the experiment, cattle are fed diets with 50% concentrate and 50% roughage (Step 1), which is fed for a period of 5 days. The proportion of concentrate is increased in a stepwise fashion, such that sequential diets each are fed for 5 days (Steps 2, 3, and 4). The final finishing diet consists of 10% corn silage as the roughage source, approximately 6-8% supplement, and the balance as flaked corn, and is fed on day 21 and until the trial is terminated after 120 to 150 days on feed. Diets are formulated to contain 33 grams/ton monensin, and during the final 28-42 days on feed contain 25 g/ton ractopamine Steam-flaked corn is processed daily. Diets are prepared fresh daily and delivered each morning to feed bunks. Grains (commodity and EFC) and forages (conventional commercial hybrid or EFC) are incorporated directly into the total mixed rations on a daily basis and blended thoroughly.

Data Collection Methods and Variables:

Bodyweights: Full pretreatment bodyweights of individual animals are determined on day 1. Interim body weights (approximately days 28, 56, 84, and 112) and the terminal body weight are captured for pens of animals.

Feed Consumption: Experimental diets are fed starting on day 1 of the study and continue until the study is terminated. The amount of feed delivered to each pen is recorded daily. Excess residual feed is removed on weigh days and as required to ensure fresh feed is maintained in the bunks. Quantities of the forage to be delivered to each pen are weighed.

Weights of unconsumed feed remaining in feed bunks are measured as required, but minimally on interim weigh days and on the final day of the study. Feed refusals may also be measured at other times at the discretion the Clinical Investigator (e.g., fecal contamination, spoilage, etc.). Dry matter determinations are performed on the composited samples of unconsumed feed at intervals. Total quantities of feed delivered (as-fed basis) to each pen during a specific interval of time are computed.

Growth Performance: Average daily gain is computed for each pen of cattle. Total dry matter intake for each pen is recorded, and gain efficiency is computed as ADG divided by daily intake per animal of feed dry matter. Dry matter intakes, rates of gain, and feed efficiencies for each pen are computed at approximately 28-day intervals and for the duration of the study.

Carcass Characteristics: On the day of harvest, animals are removed from their pens as a group, weighed using a group scale, and loaded onto trucks for transport to a commercial abattoir. Carcasses are identified by order of harvest at the abattoir. Hot carcass weight and incidence and severity of liver abscesses are recorded on the day of harvest. After 24 to 48 hours of refrigeration, marbling score, longissimus muscle area, subcutaneous fat thickness ($12^{th}$ rib), incidence of dark-cutting beef, USDA Yield Grade, and USDA Quality Grade are recorded for each carcass.

Example 5

Site and Extent of Digestion of Diets Containing Corn Grain or Corn Derived From an Enogen® Feed Corn Hybrid Objectives:

1) Compare site and extent of digestion of dry matter, organic matter, starch, neutral detergent fiber (NDF), acid detergent fiber (ADF), nitrogen, and lipid within finishing diets comprised of corn and corn silage; and
2) Measure liquid dilution rates and microbial protein synthesis in cattle fed diets consisting of combinations of corn grain and corn silage.

Study Methods:

Study Animals. The study utilizes 12 multicannulated steers (ruminal, duodenal, ileal) steers with average body weight of approximately 500 lb. Steers are fitted with ruminal, duodenal (double L; 6 cm posterior to pyloric sphincter) and ileal (double L; 10 cm anterior to the ileocecal junction) cannulae. Steers are housed in box stalls equipped with individual feed bunks and waters.

Study Design. The experiment consists of a replicated 4×4 Latin square design with a 2×2 factorial arrangement of treatments. Factors consist of 1) grain source (mill run or Enogen® Feed corn (EFC)), and 2) forage source (commercial hybrid commonly used for corn silage production or EFC silage hybrid). The experiment consists of four 15-day periods, each including a 10-day adaptation period and a 5-day sampling period.

Experimental Diets. Diets are mixed daily and offered to steers ad libitum at approximately 8:00 a.m. Diets contain (dry matter basis) approximately 10% corn silage, 84% corn, and 6% supplement.

Collection, Processing, and Analyses of Diets, Orts, Digesta and Feces.

Chromic oxide (10 g) is mixed daily into individual diets on days 4 through 13 as a marker to determine diet digestibility. On day 15, a 200-mL solution containing 3 g of CoEDTA is pulse dosed through the ruminal cannula at 8:00 a.m. to estimate liquid passage rate. On days 11 through 14, a fixed percentage of daily orts are subsampled and composited by period. Diet samples are collected after mixing on days 10 through 13 and composited by period on an equal weight basis. The 15th day of each period is used to collect ruminal fluid for measurement of pH, volatile fatty acids (VFA), and passage rate. Duodenal (~300 mL) and ileal (~200 mL) chyme and fecal grab samples (~300 g wet basis) are collected three times daily on days 11 through 14. Samples are collected at 8-hour intervals, with collection times advanced 2 hours each day to obtain a profile representing a 24-hour cycle post-feeding. Duodenal, ileal, and fecal samples are frozen immediately at 4° C. Samples of digesta and feces are composited for each steer at the end of each collection period. Diet, orts and fecal samples are dried for 4 d at 55° C., air equilibrated, and then ground using a 1-mm screen (No. 2 Wiley mill, Arthur H. Thomas Co., Philadelphia, Pa.). Digesta samples are lyophilized (Virtis Genesis model 35EL) before being ground through a 1-mm screen in a Wiley mill. Diet, orts, digesta and feces are analyzed for dry matter (24 hours at 105° C.), organic matter (600° C. for 2 hours), nitrogen (nitrogen analyzer, LECO FP-2000; St. Joseph, Mich.), starch, free glucose (using a Technicon Autoanalyzer III), and for chromium. Approximately 500 mL of ruminal fluid is collected once daily on days 11 through 14 to estimate ruminal microbial protein synthesis. Samples are blended to dislodge particle associated bacteria and strained through 8 layers of cheesecloth before being frozen at 4° C. Collection times are advanced 6 hours each day to obtain a sample at each 6-hour interval in a 24-h cycle. Ruminal microbial cells are isolated from ruminal contents by differential centrifugation, lyophilized, and analyzed for dry matter, organic matter, and nitrogen. Cytosine concentrations of microbial cells and duodenal samples are measured. The proportion of duodenal digesta of microbial origin are determined by dividing the duodenal cytosine flow by the ratio of microbial cytosine:nitrogen. Feed nitrogen flow is calculated by subtracting total nitrogen flow from microbial nitrogen flow, thus including endogenous nitrogen contributions. True organic matter fermented in the rumen is calculated as organic matter intake minus total organic matter reaching the duodenum, correcting for microbial organic matter reaching the duodenum. Samples of ruminal fluid are collected at 0800 on d 15 and subsequently at 2, 4, 6, 8, 12, 18, and 24 h after feeding. Ruminal fluid is strained through four layers of cheesecloth and analyzed for pH at the time of sampling using a portable pH meter. Ruminal fluid (8 mL) is added to 2 mL of 25% (wt/vol) metaphosphoric acid and frozen for later analysis of VFA and ammonia. Approximately 20 mL of strained ruminal fluid are placed into scintillation vials and frozen for later analysis of cobalt. Cobalt is measured in ruminal fluid after being thawed and centrifuged at 30,000×g for 20 minutes using atomic adsorption spectrophotometry. Samples of acidified ruminal fluid are thawed, centrifuged at 30,000×g for 20 min, and analyzed for VFA by gas chromatography (Agilent 7890a gas chromatograph equipped with 15 m Nukol column) and for $NH_3$ using a Technicon Autoanalyzer III (Bran and Luebbe, Elmsford, N.Y.).

Statistical Analyses.

Intake, flow, and digestion data are analyzed using individual animal as the experimental unit with PROC MIXED of SAS. The model includes effects of flaked grain source, silage source, and the interaction between grain source and silage source. Random effects include steer and period. Volatile fatty acids, $NH_3$, and pH data are analyzed as repeated measures using the compound symmetry covariance structure of PROC MIXED of SAS. The model statement includes effects of flaked grain source, silage source, hour, and all interactions. The random statement includes effects of steer and period and steer×period×grain source×silage source. The repeated measure is defined as the hour within period×steer×grain source×silage source. To determine liquid passage rates, concentrations of Cobalt at 0, 2, 4, 6, 8, 12, 18, and 24 h are transformed to natural logarithms and regressed on time for individual steers using the REG procedure of SAS. The slopes (estimates of passage rates) are analyzed using the MIXED procedure of SAS as previously described Example 6

Backgrounder Beef Cattle Study with Enogen® Feed Corn

Backgrounder cattle (sometimes called stocker cattle) are animals in an intermediate stage between weaning (typically occurring between 400 and 550 pounds) and finishing on the feedlot. These animals are traditionally fed a diet high in forage such as pasture, although supplementation is sometimes used as well.

Objective:

To determine the growing calf response to Enogen® Feed corn, containing an alpha amylase enzyme trait, when fed as whole shelled corn (WC) or dry rolled corn (DRC).

Experimental Procedures:

Four hundred and twenty-six crossbred steers (average weight 538 pounds) were transported from Lazbuddie, Tex. to the Beef Stocker Unit at Kansas State University (KSU). A 2×2 factorial design was employed with two types of corn (Enogen® vs. Yellow corn #2) and two levels of corn processing (WC vs. DRC). Steers were fed a total mixed ration (TMR) once a day for 76 days followed by a 14-day gut fill period (90 days total).

The four treatment diets were formulated to provide 51 Mcal NEg (Net energy for gain)/100 lbs. Details of the TMR are below in Table 12.

TABLE 12

Experimental diets.

| Ingredient | DM % |
|---|---|
| Corn (variety × processing)[1] | 28.57 |
| Supplement | 6.43 |
| Alfalfa Hay | 17.50 |
| Prairie Hay | 17.50 |
| WDGS[2] | 30.00 |
| 100% DM (dry matter) Basis | |
| Dry Matter, % | 60.30 |
| Protein, % | 16.08 |
| Calcium, % | 0.85 |
| Phosphorus, % | 0.41 |
| Salt, % | 0.32 |
| Potassium, % | 1.09 |
| Magnesium, % | 0.22 |
| Fat, % | 0.22 |

TABLE 12-continued

Experimental diets.

| Ingredient | DM % |
|---|---|
| ADF, % | 20.59 |
| NEm[3], Mcal/100 lb | 78.81 |
| NEg[4], Mcal/100 lb | 51.13 |

[1]Corn type: Enogen ® vs. Negative yellow #2 and fed as either whole shelled (WC) or dry rolled corn (DRC)
[2]Wet Distillers Grains with Solubles
[3]Net energy for maintenance
4Net energy for gain Results:

Steers were assessed for Initial body weight (BW), final BW, average daily gain (ADG), dry matter intake (DMI), and Feed:Gain (F:G). The results are shown in Table 13 below.

TABLE 13

Dry lot performance.

| Item | Enogen ® WC | Yellow #2 DRC | WC | DRC | SEM | P-Value |
|---|---|---|---|---|---|---|
| Initial BW (lbs) | 539 | 538 | 539 | 537 | 1.08 | 0.77 |
| Final BW (lbs) | 850 | 851 | 838 | 847 | 4.29 | 0.10 |
| ADG | 3.42 | 3.43 | 3.29 | 3.41 | 0.04 | 0.09 |
| DMI | 20.4 | 20.5 | 21.3 | 20.8 | 0.37 | 0.09 |
| F:G | 5.97 | 5.97 | 6.49 | 6.10 | 0.11 | 0.01 |

Summary:

1. The final body weights and ADG tended to be greater ($p<0.10$) for calves fed Enogen® Feed corn.
2. DMI tended to be lower ($p<0.09$) for calves fed Enogen® Feed corn.
3. The feed efficiency (F:G) of calves receiving Enogen® Feed corn was improved by 5.5% ($p<0.01$).

Example 7

Combined Enogen® Feed Corn Grain and Enogen® Feed Silage Diet in Backgrounder Beef Cattle The objective of this study is to compare Enogen® Feed corn containing an alpha amylase enzyme trait (EFC) to an isoline parental corn without the alpha amylase enzyme trait (Negative Isoline) when fed as corn silage and corn grain on growing Backgrounder beef cattle health and performance.

The relative value of EFC as a source of energy either as a silage and/or grain for newly arrived and growing beef cattle is unknown. Growing beef cattle diets are normally comprised of greater quantities of roughage and grain processing industry byproducts with approximately one-third the DM intake consisting of corn or other cereal as a source of energy.

Experimental Design—Performance Study:

The trial is initiated at the Kansas State University (KSU) Beef Stocker Unit (KSBSU), and includes 32 pens (8 for each treatment) comprised of 12-14 animals each, and lasts approximately 76 days in addition to a 14-day gut fill equalization period (90 days total). The four treatment diets are formulated to provide 50 Mcal NEg/100 lbs. Diets are similarly designed following a 2×2 factorial arrangement of treatments with factors of +alpha amylase/−alpha amylase corn silage and +alpha amylase/−alpha amylase corn grain; Table 14). Individuals are stratified by weight within their block (each load) and randomly assigned to pens. Treatments are then randomly assigned to pens.

TABLE 14

| Diet | |
|---|---|
| Ingredient | DM Percentage |
| Corn[1] | 38.5 |
| Supplement | 7.50 |
| Alfalfa Hay | 7.00 |
| Prairie Hay | 7.00 |
| Corn silage | 40.00 |
| Total | 100 |
| Item | 100% DM Basis |
| Dry Matter, % | 54.60 |
| Protein, % | 12.86 |
| Calcium, % | 1.05 |
| Phosphorus, % | 0.32 |
| Salt, % | 0.40 |
| Potassium, % | 0.94 |
| Magnesium, % | 0.19 |
| Fat, % | 3.30 |
| ADF, % | 16.66 |
| NEm, Mcal/100 lb | 78.04 |
| NEg, Mcal/100 lb | 50.36 |

[1]Corn silage and corn grain (Enogen) vs Negative isoline corn silage and corn grain 1) Description of Animals:

Approximately 400 crossbred female beef calves weighing approximately 500 lbs. are obtained and transported via commercial truck to the KSU Beef Stocker Unit. Upon arrival all animals are visually examined to assess health status, including respiratory, locomotion and digestive systems. Any animals experiencing health issues are immediately removed from the study. All animals are tested for BVDV-PI status. If positive, the animal is removed from the study.

2) Preventative Medical Requirements:

Approximately 24 hours post-arrival, cattle are processed with standard health protocols which include modified live viral (Infectious Rhinotracheitis, Bovine Viral Diarrhea, Para-Influenza-3, Bovine Respiratory Syncytial Virus) vaccine, 7-way Clostridia vaccine, and an anti-parasiticide.

3) Animal Identification:

Upon arrival, all study animals are administered with a unique dangle ear tag with an RFID button tag.

4) Water

Cattle have free access to drinking water at all times.

5) Rations:

Diets are formulated to meet or exceed the recommendations for this class of animal as recommended by the National Research Council's Nutrient Requirements of Beef Cattle (NRC, 7$^{th}$ Edition, 1996). The diets are adjusted as necessary to meet the changing nutrient requirements over the 76-day study period. The composition of the diets and all diet changes are recorded.

6) Feed and Bunk Sampling

Feed and bunk samples are collected on a weekly basis and composited for analysis.

7) Diet Adaptation and Feeding:

Calves are fed their respective treatment diets once daily, and the amounts of feed delivered at each feeding to each pen are recorded.

8) Health Treatments:

Trained employees at the KSBSU are responsible for identifying clinically ill animals, moving them to the treatment area and administering appropriate treatments. Each pen is observed at least twice daily to identify clinically ill animals. Each animal that is identified as being ill is moved to the treatment area. Animals with a clinical illness score greater than 1 and a rectal temperature greater than or equal to 104° F. and more than 72 hours post arrival are treated. Treatments are based on the KSBSU normal treatment protocol shown below (Table 15) Animals are returned to their pen of origin after treatment, and any animal treated three times for BRDC is designated as "chronic" and removed from the study.

TABLE 15

| Clinical Illness Score | | |
|---|---|---|
| Clinical Illness Score (CIS) | Definition | Clinical Appearance |
| 1 | Normal | Normal/healthy |
| 2 | Slightly Ill | Mild depression/gaunt |
| 3 | Moderately Ill | Severe depression/labored breathing/ocular or nasal discharge |
| 4 | Severely Ill | Moribund/near death/little response to human approach |

| Treatment Protocol by Event | | | | |
|---|---|---|---|---|
| Event | Antimicrobial | Dosage | Route | Slaughter Withhold |
| 1$^{st}$ Pull | Resflor (florfenicol and flunixin meglumine) | 6 ml/cwt | SQ | 38 Days |
| 2$^{nd}$ Pull | Baytril (enrofloxacin) | 5 ml | SQ | 28 Days |
| 3$^{rd}$ Pull | Biomycin (oxytetracycline) | 5 ml | SQ | 28 Days |

9) Performance and Health Data Collection

Cattle are individually weighed upon arrival (day −1), initial processing (day 0), revaccination (day 14), day 48 (fecal starch grab sample) and the last day of the trial (day 90). Pen weights are recorded on a weekly basis where there is not an individual weight scheduled. Average daily gain and feed conversion are calculated for each pen for five time periods: arrival to day 14, to day 21, to day 34, to day 48, to day 62, and to day 76. Feed bunks are read by KSBSU employees daily and the amount of feed allocated is based on the bunk score from that day reflecting feed consumption since the previous feeding. Total amount of feed off-loaded to each pen is recorded at each feeding.

Morbidity, mortality, case fatality, date to first pull, and first antimicrobial treatment success rate are calculated if necessary. Morbidity is calculated as the number of animals per treatment receiving a first BRDC treatment divided by the number of animals enrolled in the treatment. Mortality is calculated as the number of animals dying from BRDC per treatment divided by the total number of animals enrolled in the treatment. Case fatality is calculated for each treatment as the number of deaths due to BRDC divided by the number of animals treated at least once for BRDC. Date to first pull is calculated using the date the animal was pulled in respect to day 0 of the trial. First antimicrobial treatment success rate is determined by dividing the number of animals treated only once for illness by the total number of animals initially treated for illness.

10) Physical Environment Measurements

Weather data, including precipitation, wind speed and direction, relative humidity, and temperature is collected by a weather monitoring station (Storm3 Waterlogger Five Parameter Weather Station, Stevens Water Monitoring Systems, Inc.) over the 56-day research period.

11) Data Analysis

Data are analyzed to assess the difference in performance and health results between the four dietary treatments. Proportion of treatment level morbidity, mortality and case-fatality are analyzed using logistic regression models.

Experimental Design—Intake and Digestibility Study:

The trial is conducted at the Kansas State University Beef Stocker Unit (KSBSU) concurrent with the performance study described above. Four beef crossbred steers weighing 450-500 lbs. are used to conduct the intake and digestibility study (Wang et al., 2016. *J. Anim. Sci.* 94-1159-1169). The steers are individually housed in an outdoor facility. Using the same treatment diets listed above, one steer is randomly assigned to each treatment for a total of 4 steers.

1) Latin-Square Design

Four beef crossbred steers are used to determine in vivo digestibility of the test diets. The study lasts 60 days with four 15-day periods to complete a Latin square design. Each period consists of a 10-day adaptation period, 4 days of fecal sampling, and 1 day of collecting ruminal digesta samples.

2) Ruminal Digesta Samples

Ruminal digesta samples are taken at the end of each period to determine digestibility of the treatment diets. Samples are also analyzed for the proportion of marker to determine liquid dilution rates. Concentrations of acetate, propionate, butyrate, and lactate are analyzed and calculated.

3) Fecal Samples

Timed fecal grab samples are analyzed to determine the concentration of marker present.

4) In Vitro Analysis

In vitro fermentation is used to determine in vitro dry matter digestibility (IVDMD), in vitro organic matter digestibility (IVOMD), and gas production associated with the four treatment diets.

Example 8

Impact of Enogen® Feed Corn Silage or Grain on Growing Beef Cattle Performance and Digestion Objective: To evaluate Enogen® Feed Corn (EFC) grain in backgrounding diets containing 40% corn grain and to evaluate EFC corn silage (with equivalent grain assuming silage is 50% grain on a dry matter [DM] basis).

Experimental Procedures

Silage: Irrigated corn grown at the Eastern Nebraska Research and Extension Center is used for harvesting silage and dry grain. Silage harvest was targeted at 37-38% DM or approximately ¾ milkline Each load of silage was weighed at delivery and sampled for initial DM content. During feedout, silage is sampled at the face weekly for DM analysis. Samples are retained by week for subsequent nutrient, pH, and organic acid content on monthly composites. All material removed for feeding is weighed as-is and the weekly DM percentages used for DM amount fed. Grain was produced under identity-preserved protocols and stored as whole grain in separate bins. As needed, grain is delivered and processed as dry-rolled corn under identity-preservation.

Growing Study:

Cattle Background: All steers are received as weaned calves at the University of Nebraska Eastern Nebraska Research and Extension Center near Mead, Neb. Calves are received for 3 to 4 weeks prior to the experiment to ensure all calves are healthy. Calves may be grown over winter prior to experiment to ensure health and readiness. Animal handling and space for this experiment are in accordance to the Guide for the Care and Use of Agricultural Animals in Agricultural Research and Teaching (FASS, First Revised Edition, January 1999). All procedures outlined as part of this study are in compliance with the University of Nebraska animal care committee.

Design and Allotment

Steers are limit-fed at an estimated 2% of body weight (BW) a 50% alfalfa, 50% wet corn gluten feed (WCGF) diet for 5 days prior to weighing. Weights are collected on individuals on two consecutive days to minimize gut fill effects and get an accurate initial body weight.

This study utilizes 576 steers (12 steers/pen). Steers are assigned randomly to pens based on the first day weight. Blocking criteria may be used depending on range in body weight. Pens are assigned randomly to one of 6 treatments described below. This study is designed as a completely randomized design (or randomized block design if blocking criteria are required) with 6 treatments arranged as a 2×2+2 factorial arrangement of treatments. Pen is the experimental unit, and there are 8 replications per simple effect treatment, or a total of 48 pens with 6 treatments.

Diets and Feeding

Treatment diet composition is described Table 16. The treatment structure is organized as a 2×2 factorial along with 2 additional comparison treatments. In the factorial arrangement, factors include silage with or without Enogen® alpha amylase expression trait (EFC) and either kernel processed (2 mm) or not. An additional 2 treatments allow for evaluation of corn grain used in backgrounding diets with forage. The 40% inclusion of grain is identical to the 40% grain inclusion when 80% corn silage is fed, assuming 50% corn grain and 50% forage in corn silage.

All diets contain 15% distillers grains to provide sufficient dietary rumen undegradable protein (RUP) to meet protein requirements and 5% dry meal supplement. The primary components in the meal supplement are calcium, urea for rumen degradable protein, trace mineral premix, vitamin ADE premix, and Rumensin® at targeted levels. The carrier for the meal supplement is finely ground corn. Diets are formulated to provide similar Ca and appropriate Ca:P ratios. The final diets provide 200 mg/steer daily of Monensin. Steers are fed once daily and diets mixed using Roto-mix feed trucks.

TABLE 16

Diets fed to growing steer calves for approximately 84 days to evaluate use of EFC silage or corn grain.

| Trait: Kernel processing: Silage or grain: | CON[1] +KP Silage | EFC +KP Silage | CON No KP Silage | EFC No KP Silage | CON Grain | EFC Grain |
|---|---|---|---|---|---|---|
| Corn Silage-CON KP | 80 | — | — | — | — | — |
| Corn Silage-EFC KP | — | 80 | — | — | — | — |
| Corn Silage-CON no KP | — | — | 80 | — | — | — |
| Corn Silage-EFC no KP | — | — | — | 80 | — | — |
| Dry-rolled corn-CON | — | — | — | — | 40 | — |
| Dry-rolled corn-EFC | — | — | — | — | — | 40 |
| Grass hay | — | — | — | — | 40 | 40 |
| Wet distillers grains | 15 | 15 | 15 | 15 | 15 | 15 |
| Supplement[2] | 5 | 5 | 5 | 5 | 5 | 5 |

[2]CON, conventional corn without Enogen® alpha amylase trait.

[1]Supplement to provide Rumensin (200 mg/steer daily) and minerals and urea to ensure protein, mineral, and vitamin requirements are met.

Measurements

Cattle are weighed on two consecutive days at the beginning of the trial and two consecutive days on approximately day 84 for ending live BW. Steers are limit-fed at 2% of body weight the same diets fed for collection of initial and ending body weights to equalize gut fill across cattle and treatments.

Performance traits include dry matter intake, average daily gain (using limit-fed initial weight and ending body weight), and feed efficiency.

Example 9

Enogen® Feed Silage Quality Study

Studies were carried out to evaluate a number of silage quality parameters in Enogen® Feed silage as compared with conventional corn silage not containing an alpha amylase trait. Silage prepared from Syngenta Enogen® corn containing an alpha amylase trait had a number of improved properties as compared with control silage made from Golden Harvest (GH)/NK hybrids (similar genetic background) or competitor corn hybrids. Discriminant analysis indicated that the nutritional characteristics of Enogen® Feed silage can be distinguished from the controls based on the presence of the alpha amylase trait, rather than the genetic background (data not shown).

Silage was prepared from whole corn plants cut about 6 inches above-ground; the material was then chopped, and small scale samples were collected in bags and vacuum sealed. Samples were allowed to ferment for 60 to 75 days before analysis. Some samples were excluded due to being too dry at collection or for failing to ferment effectively. Final sample counts included for analysis were: 165 Enogen® Feed silage samples, 160 GH/NK non-Enogen® samples, and 105 competitor hybrid samples without an alpha amylase trait.

Near-infrared reflectance (NIR) spectroscopy was used to evaluate a number of silage nutritional characteristics. Starch and sugar characteristics were also assessed using chemical analysis, and in situ starch digestibility in the rumen was determined by measuring the disappearance of starch from silage samples incubated in a porous bag in the rumen for 7 hours.

As determined by NIR, there were no meaningful differences in the concentrations of protein, fat, lignin, ash, lactic acid, or acetic acid or in the pH of the silage produced from Enogen® Feed corn as compared with the non-Enogen® silage from GH/NK or competitor corn hybrids lacking the alpha amylase trait (data not shown).

Significant differences were identified in starch and sugar characteristics of Enogen® Feed silage as compared with corn silage not containing an alpha amylase trait. Two important factors influencing starch availability to the animal are particle size and digestibility. As shown in FIG. 1, using chemical analysis there were similar levels of total starch between Enogen® Feed silage and non-Enogen® silage. However, Enogen® Feed silage had a higher level (199.5% increase) of small particle starch (determined by diffusion through a 50 μM pore), which may be more quickly available in the rumen, and therefore may provide more immediately available energy. In addition, a 14% increase in rumen starch digestion after 7 hours in situ (isSD7) was observed, suggesting better digestibility of available starch with Enogen® Feed silage.

Figure 2:
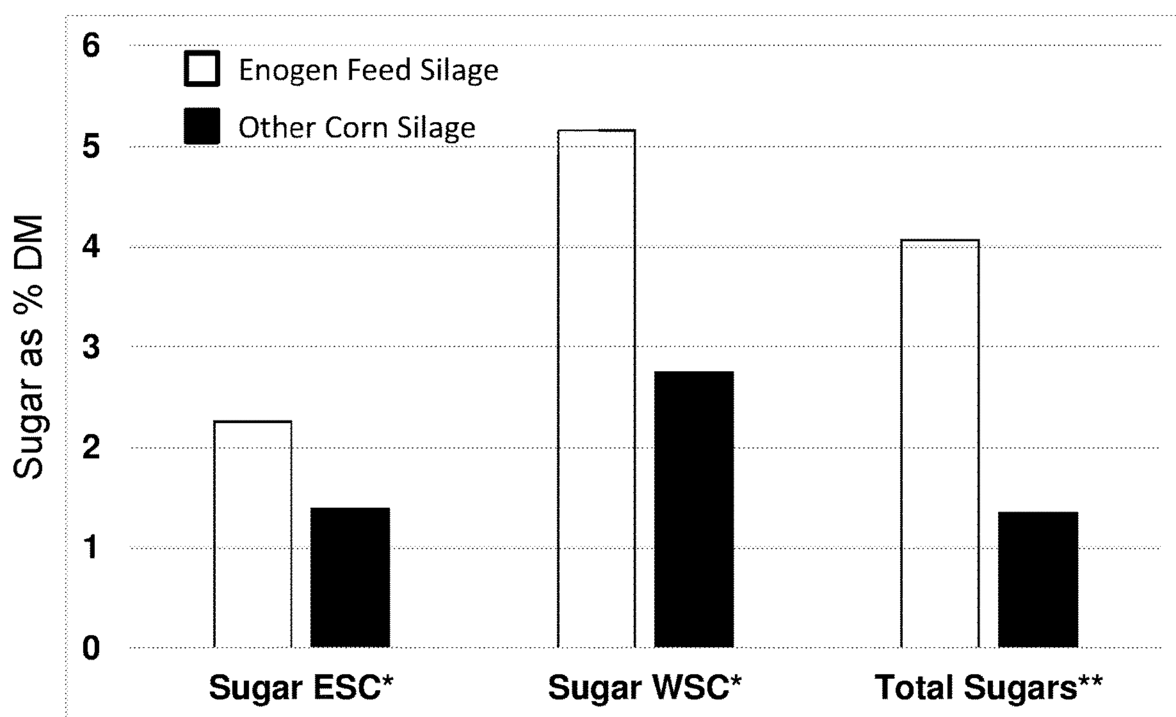
FIG. 2 is a bar graph showing sugar characteristics of Enogen® Feed silage as compared with silage from corn not containing an alpha amylase trait. Ethanol soluble carbohydrates ("Sugar ESC") represents carbohydrates that can be solubilized and extracted in 80% ethanol. Water soluble carbohydrates ("Sugar WSC") are carbohydrates that can be solubilized and extracted in water. Sugar ESC and Sugar WSC were both determined by near-infrared reflectance (NIR) spectroscopy. Total Sugars was measured using analytical chemistry and reflects the sum of total glucose, fructose, lactose, sucrose and mannitol.

Sugar is another source of rapidly available energy to the animal. Silage tends to have relatively low natural concentrations of sugar, but as shown in FIG. 2, Enogen® Feed silage had a significantly higher level (201%) of total sugars as determined by analytical chemistry methods as compared with conventional corn silage without an alpha amylase trait, with the potential for more available energy to the animal and rumen microbes. Both Ethanol Soluble Carbohydrates (ESC) and Water Soluble Carbohydrates (WSC) as determined by NIR were significantly higher in Enogen® Feed silage as compared with either GH/NK silage or competitor hybrid silage lacking an alpha amylase trait. Further, total sugars (glucose, fructose, sucrose, lactose and mannitol) as measured by chemical analysis showed the same pattern.

Fiber characteristics of the silage were also determined by NIR. Fiber digestibility is positively correlated with dry matter intake, because more digestible fiber is less filling to the animal as a result of faster transit time through the rumen. The animal then has the ability to consume more forage, which may positively impact performance, such as ADG or milk production. Neutral detergent fiber digestibility (NDFd) is a measure of fiber digestibility taken at various time intervals, and is often used to compare the feeding value of forages. High NDFd silage allows for greater dry matter intake potential, and therefore the potential to feed more silage to the animal.

Figure 3:
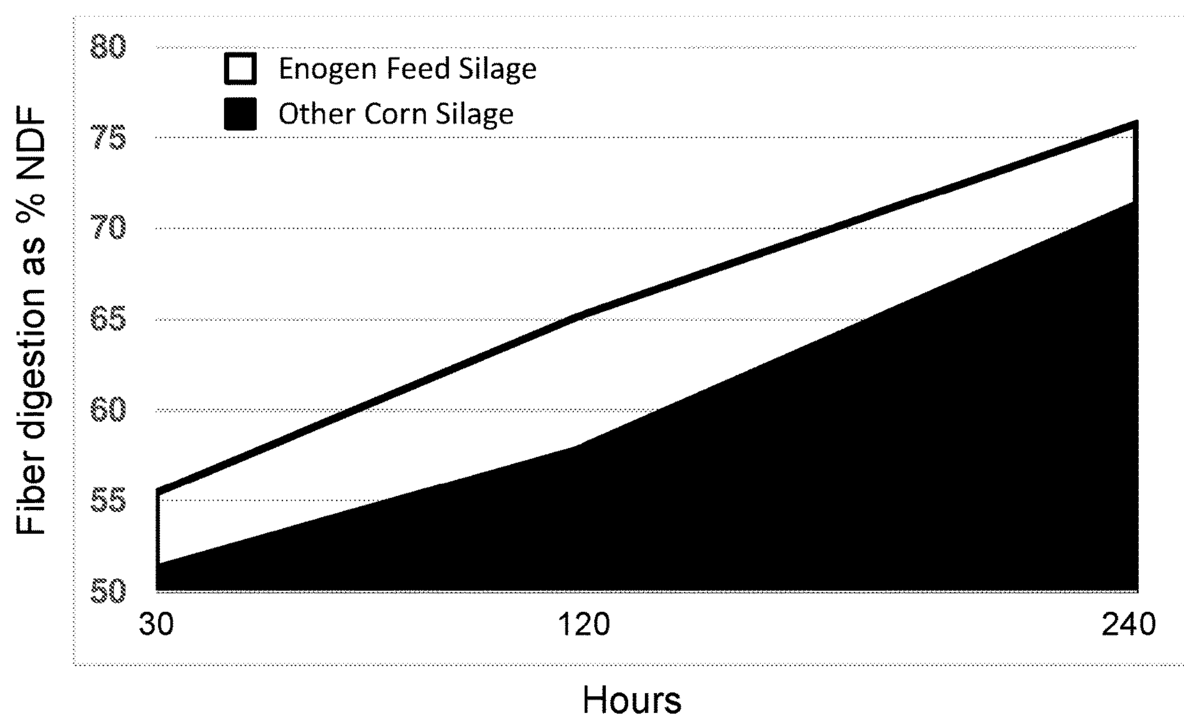
FIG. 3 is a graph showing neutral detergent fiber digestibility (NDFd) of Enogen® Feed silage as compared with silage from corn not containing an alpha amylase trait. NDFd was assessed by NIR from a time period from 30 to 240 hours. Differences were significantly different at all time points.

In this study of silage quality, Enogen® Feed silage was predicted by NIR to have a higher NDFd, an important indicator of fiber digestibility, than conventional corn silage. As shown in FIG. 3, Enogen® Feed silage had increased NDFd values as determined at several time points as compared with non-Enogen® corn silage not containing an alpha amylase trait: an 8.2% increase (30 hours), 12.6% increase (120 hours), and 6.2% increase (240 hours). Values were significantly different at all time points. Conversely, Enogen® Feed silage is predicted by NIR to have an 18.5% (120 hour) and 17.4% (240 hours) decrease in undigestible neutral fiber (uNDF) as compared with conventional corn silage (data not shown).

Moreover, as predicted by NIR, there was 6.4% increase in total tract neutral detergent fiber digestibility (TTNDFd) of Enogen® Feed silage as compared with conventional corn silage (data not shown). TTDNFd offers a holistic view of fiber digestibility by assessing the rate of fiber digestion, the rate of fiber passage, and indigestible fiber content. A higher TTNDFd value suggests better fiber digestibility and dry matter intake, which may support enhanced animal performance.

In summary, this study points to Enogen® Feed silage as having an increased concentration of small particle starch, resulting in improved starch digestibility. This starch characteristic along with a greater level of sugars provide more readily available energy sources to the animal and ruminant microbes, which may result in improved animal performance. Further, improved fiber digestibility in Enogen® Feed silage may result in greater dry matter intake, which again supports enhanced animal performance, which in the case of this study is predicted to be about 2 to 5 lbs/head/day increased milk production based on analysis with a commercial software package (NDS Professional, available for download on the World Wide Web at rumen.it/en/ndspro) commonly used by professional animal nutritionists.

Example 10

Evaluation of Fermentation, Nutritive Value, and Aerobic Stability of Enogen® Feed Corn Silage Stored at Variable Temperatures or Treated with Different Inoculants/Chemical Stabilizers Objectives:

To evaluate the fermentation, ruminal starch digestibility and aerobic stability of Enogen® Feed Corn (EFC) silage vs control silage as affected by storage length under 1) different storage temperature regimes or 2) different pre-storage treatment with inoculant or chemical stabilizer.

Materials and Methods:

Corn hybrids are supplied by Syngenta and planted and managed under normal agronomic practices at the University of Delaware Farm. Plots are approximately 8 to 12 rows and 400-600 ft. long. Whole plant dry matter (DM) was harvested using a pull-type harvester (John Deere 3975, Moline, Ill.) equipped with a mechanical processor (roller gap setting of 1.40 mm). Corn plants were chopped at a target of 34-36% DM and a theoretical length of cut of 19 mm and packed in 7.5 L lab silos at a density of about 230 kg of DM/m$^3$ (about 44 lb as wet weight or 15 lb of DM/ft$^3$).

Experiment 1 Temperature Effect:

Five individually prepared replicates of the following treatments were packed for storage for different lengths of time and temperatures (6 trt×5 reps×3 time points=90 silos):

1) Control hybrid stored at 22° C. (72° F.)
2) Enogen® Feed corn stored at 22° C.
3) Enogen® Feed corn treated with LB500* stored at 22° C.
4) Control hybrid stored at 40° C. (104° F.)
5) Enogen® Feed corn stored at 40° C.
6) Enogen® Feed corn treated with LB500* stored at 40° C.

*LB500=final application rate of 400,000 cfu of *Lactobacillus buchneri* 40788+100,000 cfu of *Pediococcus pentosaceus* 12455 (Lallemand Animal Nutrition).

Silos from treatments 1-3 are stored at lab room temp of about 21-22° C. for 30, 120 and 240 d. Silos from treatments 4-6 are stored at an elevated temperature of about 40° C. for days 0 to 120 d, but then are stored at a lower (but still elevated) temperature of about 32° C. until the 240 d opening.

Experiment 2 Effect of Inoculant/Stabilizer:

Five individually prepared replicates of the following treatments were packed for storage for different lengths of time after treatment with inoculant or chemical stabilizer, all at 22° C./72° F. (6 trt×5 reps×3 time points=90 silos):

1) Control hybrid untreated
2) Control hybrid with chemical stabilizer*
3) Control hybrid+LB500**
4) Enogen® hybrid untreated
5) Enogen® hybrid with chemical stabilizer
6) Enogen® hybrid+LB500**

**LB500=final application rate of 400,000 cfu of *Lactobacillus buchneri* 40788+100,000 cfu of *Pediococcus pentosaceus* 12455 (Lallemand Animal Nutrition).

Sampling and Analysis:

At each opening (30, 120 and 240 d) for each experiment, silo weights are determined and used with the DM content of silages to determine DM recovery. From previous experience, long term storage of silage samples in lab silos often results in a lack of viable yeasts because the silos are extremely air-tight (more so than what occurs in commercial silos). Thus, during storage, silos stored for 120 and 240 d openings, are subjected to a controlled air-stress of 4 h/wk for the final 6 wks of storage. At all silo opening the aerobic stability of corn silages is determined. About 3±0.01 kg of representative corn silage from each silo is returned to the same cleaned silo. A thermocouple wire is placed in the geometric center of each sample mass and temperatures is recorded every 30-min using a data logger (DataTaker DT85, Thermo Fisher Scientific Australia, Pty). Ambient temperature is recorded from a thermocouple wire in an empty bucket. Buckets are covered with two layers of cheesecloth and exposed to air in the laboratory (22±1° C.). Aerobic stability is calculated as the number of h before the temperature of the silage mass rises 3° C. above baseline temperature.

The DM content of all samples is determined by drying in a 60° C. forced-air oven for 48 h. A portion of each dried sample is ground using a Udy Cyclone Sample Mill (Udy Corp., Fort Collins, Colo.) to pass through a 1-mm screen and analyzed for neutral detergent fiber (NDF). Acid detergent fiber (ADF) is quantified on dried ground samples according to known procedures, with the modification that that the fiber residue from the ADF is recovered on a 1.5 μm particle retention 7 cm Whatman filter in a California Buchner Funnel (934-AH Whatman Inc., Clifton, N.J.) instead of a Gooch crucible, to allow for better filtration. Total N is determined by combustion of the sample (LECO CNS 2000 Analyzer, LECO Corporation, St. Joseph, Mich.) and crude protein (CP) is calculated by multiplying the resulting total N by 6.25. Soluble protein (% of CP) is determined. A separate portion of the dried samples is ground to pass through a 3-mm screen and analyzed for starch and 7 h in vitro ruminal digestibility of starch. The concentrations of ash, ADF, NDF, CP, soluble N, starch and starch-D are analyzed by Cumberland Valley Analytical Services, Hagerstown, Md.

Representative samples of wet forages and silages are mixed with sterile quarter strength Ringers solution (Oxoid BR0052G, Oxoid, Unipath, Ltd., Basingstoke, UK) and homogenized for 1 min in a Proctor-Silex 57171 blender (Hamilton Beach/Proctor-Silex Inc., Washington, N.C., USA). The pH is determined on fresh water extracts. The numbers of total lactic acid bacteria, are determined by pour-plating 10-fold serial dilutions on de Man, Rogosa, and Sharpe agar (CM3651, Oxoid, Unipath, Basingstoke, UK). Plates are incubated anaerobically at 32° C. for 48 to 72 h. Total yeasts and molds are determined by pour-plating 10-fold serial dilutions on malt extract agar (CM0059, Oxoid, Unipath, Basingstoke, UK). These plates are incubated aerobically at 32° C. for 48 to 72 h prior to enumeration. Portions of the water extracts are frozen prior to analyses. Lactic and acetic acids, 1-2 propanediol, (1, 2 PD) and ethanol are determined on the water extracts via HPLC Ammonia-N is determined on the water extracts by a phenol-hypochlorite method. The water soluble carbohydrate (WSC) is quantified by a colorimetric procedure.

Analyses by plant material and timing (Table 17):

TABLE 17

| Item | Fresh corn plant[1] | Silo openings[2] Days 30, 120, and 240 |
|---|---|---|
| DM | X | X |
| pH | X | X |
| N | X | X[3] |
| Sol-N | X | X[3] |
| ADF | X | X[3] |
| NDF (om) | X | X[3] |
| Starch | X | X[3] |
| Starch-D, 7 h in vitro | X | X[3] |
| Ash | X | X[3] |
| Lactic, acetic, propionic, and butyric acids, ethanol, and 1,2 PD | NA | X |
| NH3-N | X | X |
| WSC | X | X |
| LAB | X | X |
| Yeasts & molds | X | X |
| Aerobic Stability | NA | X |
| DM Recovery | NA | X |

[1]5 replicates each for isoline and Enogen ® Feed corn = 10 samples
[2]6 trt × 5 reps × 3 openings = 90 samples
[3]Analyses completed by qualified laboratory Statistics:

The data from each silo opening are analyzed separately as a completely randomized design. The model includes the fixed effect of treatment. Data are analyzed using the proc glm of the software SAS 9.3 (SAS Institute Inc., Cary, N.C.) and differences reported as significant when P≤0.05. When the overall P-value is significant, means are separated by Tukey's test (P≤0.05).

Example 11

Dairy Cow Study with Enogen® Feed Silage

A study was carried out to evaluate the impact of feeding Enogen® Feed silage to dairy cows on milk production, milk quality and body condition scores (BCS).

Experimental:

Dairy cows were housed in pens based on lactation stage/performance, and pen-fed a total mixed ration (TMR) tailored to the nutritional needs of the cows in that pen. The animals were not administered bovine somatotropin.

The silage was produced on farm from Enogen® Feed corn or conventional corn not containing an alpha amylase trait. The silage was fermented for 3 months prior to use. Data was collected from animals fed a TMR containing a conventional corn silage without an alpha amylase trait for 30 days (OFF Enogen® Feed silage period). Afterwards, the animals were transitioned from conventional silage to Enogen® Feed silage by feeding the two silages in a 50:50 ratio for 12 days. The animals were then switched to 100% Enogen® Feed silage as the silage component of the TMR for 85 days (ON Enogen® Feed silage period).

Milk yield was measured daily for each cow through an electronic milk parlor system. Pen dry matter intake (DMI) was measured daily through a TMR inventory system.

Body condition scores were assessed monthly during the course of the study on 10% of cows, selected randomly from all pens. Scoring is done on a scale of 1 to 5, with a score of 1 being too lean, a score of 5 being too heavy, and a score of 3 being ideal.

The cows were divided into pens as follows: early lactation (1 pen), late lactation (2 pens), and high producing (2 pens). Rations for each pen were formulated by a professional animal nutritionist.

For the high producing cow rations, the forage composition of the TMR was as follows:

TABLE 18

| Forage composition of High Cow ration: | | |
|---|---|---|
| | Conventional silage (OFF period) | Enogen ® Feed Silage (ON period) |
| Corn silage, % DM | 44 | 42 |
| Alfalfa silage, % DM | 13 | 16 |
| Corn silage, % forage | 77% | 72% |

Rations for early and late lactation cows generally have a lower energy content as compared with the ration for high producing cows, reflected by a higher percent of the ration being in the form of forage (silage) as compared with the rations shown in Table 18. The forage content and composition of the cows in the OFF and ON periods were calculated to be similar for early and late lactation cows.

Lactation performance was assessed during the OFF and ON periods as averages across all pens (early lactation, late lactation and high producing). As can be seen in Table 19 below, dairy cows fed on Enogen® Feed silage produced more milk per day, than during the OFF period with conventional corn silage in the ration. At the same time, DMI (dry matter intake) was reduced, resulting in an improvement in feed efficiency (FE). The total number of cows and the days in milk for the herd were not significantly different between the OFF and ON periods, and therefore not expected to result in significant differences in performance, intake or feed efficiency between the two periods.

TABLE 19

| Lactation performance | | | |
|---|---|---|---|
| Average across all pens | OFF Enogen ® Feed silage | ON Enogen ® Feed silage | Difference (ON − OFF) |
| DMI[1], lb/cow/day | 58.3 | 55.7 | −2.6 |
| Milk, lb/cow/day | 79.9 | 83.7 | +3.8 |
| FE[2], Milk/DMI | 1.37 | 1.51 | +0.14 |
| Days in Milk | 170 | 174 | +4 |
| 150-day Adjusted Milk, lb/cow/day | 81.2 | 85.6 | +4.4 |

[1]Dry matter intake
[2]Feed efficiency

In addition to the amount of milk produced, the milk quality and animal body condition are important considerations. One concern with high producing dairy cows is that body condition will suffer, which may result in a long-term loss of productivity. Likewise, an increase in milk production is of limited value if milk quality is significantly reduced. In this study, milk quality and body condition scores were maintained, even in the face of higher milk production. There were no significant differences in fat, protein and milk urea nitrogen (MUN) composition of the milk produced during the OFF and ON periods (data not shown). Further, there was no change in BCS, with average scores of approximately 3 in randomly selected animals both during the OFF and ON periods (with a score of 1 being too lean, a score of 5 being too heavy, and a score of 3 being ideal).

In sum, in this study, dairy cows fed Enogen® Feed silage as part of a TMR had improved milk production, while maintaining milk quality and body condition.

Example 12

Effect of Enogen® Feed Corn Supplementation on Production and Feed Intake in High Producing Dairy Cows Objective:

To determine the effects of feeding corn silage produced from a hybrid which expresses an alpha amylase trait ("Enogen® Feed Corn" or "EFC") versus standard corn silage on feed intake and milk production in transitional, high producing dairy cows.

Planting, Harvest and Storage:

Syngenta provided seed of the EFC hybrid corn (EFC Seed) and seed of a near-isoline hybrid corn (Control Seed)) for the study in sufficient quantity to plant approximately 22 acres per hybrid at a target seeding rate of 33,000 seeds/acre. Seed was planted using a 24-row planter in the same 45 acre field. EFC silage and Control silage was harvested between 62-65% whole plant moisture and stored in segregated ag-bags inoculated with the commercial dairy inoculant LB 500.

Animals and Treatments:

Twenty-four (24) Holstein dry cows entering their second or greater lactation were blocked to treatments based on expected calving date, lactation, body condition score (BCS), and previous milk production (ME 305). Two dietary treatments were assigned at random 1) Control corn silage and 2) EFC silage. Dry cows were housed in Biocontrol Individual Feed Stations beginning ~3-4 weeks prior to expected calving, and the ration included the assigned silage treatments (Control vs EFC) during this prepartum period. Upon calving, animals were assigned to one of the two corn silage treatments within the high cow ration. Animals remain in the Biocontrol pen up to 90 days in milk (DIM). See Table 20 for treatment assignments. The entire experiment was repeated with a second group of twenty-four (24) cows as soon as possible after the Biocontrol gates begin to be available again as the first group pass 90 DIM.

TABLE 20

Experimental Design

| Treatment # and description (6 cows per group) | Silage component of TMR[1] by Feeding Period<br>Last ~ 4 weeks gestation period | Followed by Post-fresh period |
|---|---|---|
| 1 Control | Control silage | Control silage |
| 2 Gestation only | EFC silage | Control silage |
| 3 Lactation only | Control silage | EFC silage |
| 4 Whole study | EFC silage | EFC silage |

[1]Total mixed ration

Ration and Feed Delivery:

Cows housed in the commercial barn or communal pens were fed a total mixed ration (TMR) twice daily, whereas animals housed in the Biocontrol gates were fed a TMR once daily. The basal ration minus the corn silage was prepared for all pens in one load using a Roto-Mix Rotary Mixer. After the basal ration was mixed, the ration was unloaded and one-half was added to the mixer along with the Control silage. The ration was further mixed and delivered to the control pens or Biocontrol gates. The mixer was cleaned and the remaining one-half of the basal ration that was unloaded was reloaded back into the mixer along with the EFC corn silage. After mixing, the EFC treatment corn silage ration was delivered to their respective pens or Biocontrol gates.

Feed bunks were read before the daily feeding and feed calls adjusted accordingly based on residual feed remaining in the bunk. Cows were fed for slight feed refusal, a score of 1 on a 0 to 4 scale; where 0 is no feed remaining and 1 is 1-5% feed remaining Recipe mixed, feed delivered, and residual feed remaining in the bunk were recorded electronically using TMR Tracker (Digi-Star, Fort Atkinson, Wis.). To maintain consistent nutrient density the ingredient composition of the ration was adjusted at regular intervals to account for changes in dry matter content of corn silage and alfalfa silage over time.

Parameters Measured:

Dry cows' dry matter intake (DMI) was recorded daily at the individual level once in the Biocontrol gates. Upon freshening, cows were milked 3× daily and individual milk yield was recorded and stored. Milk samples were collected from each cow once weekly until 90 DIM at 3 consecutive makings and analyzed for fat, protein, and lactose percentages, somatic cell count (SCC), and milk urea nitrogen (MUN) by AgSource Laboratories (Menomonie, Wis.). Daily individual DMI was recorded from 0-90 DIM. Individual cow body weights were taken weekly during the trial. Cow events such as health, breeding, etc. were recorded in DairyCOMP 305 (DC305; Valley Agricultural Software, Tulare, Calif.). Dry matter intake per pen was calculated from daily feed delivery less feed refusals. BCS measurements were taken prior to the trial, at calving, 45 DIM and on the last day of the trial. Locomotion scores were recorded when each cow was placed into the Biocontrol gates (~30 days pre-calving) and at 0, 45 and 90 DIM. TMR and refusals were collected once weekly and frozen until analysis. On days, 0, 14, 28, and 42 fecal samples were collected and analyzed for fecal starch. Past 45 days, fecal samples were collected once a month until peak milk. Temperature at the face (12") and at 36" into each silage bag was recorded 3 times per week, probing 5 locations across the face of the silage bag for each depth. Laboratory silage stability studies were performed for four consecutive weeks.

Results.

The results showed an increase in milk production and milk feed efficiency (lb milk produced per lb feed consumed) as follows (Table 21):

| | Treatment | | 90 Day Average | | |
|---|---|---|---|---|---|
| | Pre-Fresh | Post-Fresh | Milk Volume[1] | Feed Intake[2] | Feed Efficiency[3] |
| 1. | Control | Control | 103.455 | 62.904 | 1.6555 |
| 2. | Control | EFC | 108.201 | 65.604 | 1.6783 |
| 3. | EFC | Control | 107.864 | 60.867 | 1.6321 |
| 4. | EFC | EFC | 111.364 | 59.317 | 1.7918 |

[1]lb/head/day
[2]lb DMI/head/day
[3]milk volume/feed intake

- Control pre-fresh/Control post-fresh (treatment 1) was approximately 103.5 lb milk/head/day vs EFC pre-fresh/EFC post-fresh (treatment 4) at 111.4 lb/head/day
- Difference of 7.9 lb/head/day average over 90 days lactation when EFC was fed both pre- and post-freshening
- The other 2 treatments (EFC during pre-fresh or post-fresh periods; treatments 2 and 3) gave intermediate results
- Feed efficiency for treatment 1 (Control pre-fresh/Control post-fresh) was 1.656 vs 1.792 for treatment 4 (EFC pre-fresh/EFC post-fresh).

Example 13

Dairy Performance Study: Feeding a Combination of Enogen® Feed Grain and Silage A dairy performance study is conducted at the Arlington Agriculture Research Center of University of Wisconsin-Madison. Multiparous Holstein cows in mid-lactation are used in this pen study. There are 16 pens with 8 cows in each pen, for a total of 128 cows.

The experiment begins with 2 weeks of covariate period when all cows are fed the same diet. For the subsequent 10 weeks, pens are randomly assigned one of the four diets containing different levels of Enogen® Feed corn silage or Enogen® Feed corn grain.

The four experimental dietary treatments are:

1) 40% conventional corn silage and 15% conventional corn grain (negative control)
2) 40% Enogen® Feed corn silage and 15% conventional corn grain (corn silage effect)
3) 40% conventional corn silage and 15% Enogen® Feed corn grain (corn grain effect)
4) 40% Enogen® Feed corn silage and 15% Enogen® Feed corn grain (positive control)

Samples/Response Variables to Measure:

- Dry Matter Intake: Cows are fed total mixed ration (TMR) once daily ad libitum, adjusting the amount offered to have 5-10% of refusals for each pen. Forages are dried to 60° C. for 48 h to adjust the TMR ingredient mixes for variation in dry matter (DM) every week.
- Feed ingredient: Individual feed ingredients, TMR, concentrate mix, and orts are sampled once every week and kept frozen for later analysis. Each feed ingredient samples are composited every two weeks, dried, and ground to pass 1.0 mm sieve in a Wiley mill. Samples are analyzed for crude protein (CP), neutral detergent fiber (NDF), acid detergent fiber (ADF), starch, lignin, ether extract (fat), and ash. In addition, ruminal in vitro NDF digestibility at 30 h, (NDFD30 h), ruminal in vitro starch digestibility at 7 h for the composite samples of forages, concentrate mixes (including conventional and Enogen® Feed corn silages and grains) are determined.
- Milk Production and Composition: Milk yield is measured daily for each individual cow during the course of the experiment. Cows are milked twice a day AM and PM. Milk samples for milk composition are collected on for two consecutive days (4 milkings) every two weeks. Milk samples are analyzed for fat, protein, lactose, somatic cell, and milk urea nitrogen (MUN) concentrations.
- Spot urine sample: Urine samples for each cow are collected 4 time points with 6 h interval to cover the 24 h clock. Urine samples are analyzed for purine derivative and creatinine concentration to estimate the microbial protein synthesis and urine volume.
- Blood sample: Blood samples for each cow are collected and analyzed for amino acid profile once at the end of the trial.
- Body Weight (BW) and Body condition Score (BCS): Cow BW and BCS are measured on 2 consecutive days at the beginning of the trial, during the 5th week of experimental diet, and last week of the experiment.

Example 14

Dairy Waste Production Study: Feeding a Combination of Enogen® Feed Grain and Silage A study of dairy performance, enteric methane emission, ruminal metabolism, nitrogen utilization, and nutrient digestibility is conducted at the University of Wisconsin, using lactating dairy cows fed conventional or Enogen® Feed corn silage and Enogen® Feed corn grain.

Material and Methods

Experimental design is a replicated 4×4 Latin Square (4 cows per square, 4 periods), with four 28-d periods (14-d for adaptation and 14-d for data collection) for a 16-week trial. Twenty multiparous lactating cows in mid-lactation are housed in a tie-stall barn. In addition to the four squares of non-cannulated cows, four ruminally cannulated (RC) cows are on a double cross-over design. Cows are fed once daily and milked twice daily. The four dietary treatments for the non-cannulated cows are listed below, containing different levels of Enogen® Feed corn silage or Enogen® Feed corn grain. Cows are randomly assigned within squares to the 4 dietary treatment sequences.

The four experimental dietary treatments for the non-cannulated cows are:

1) 40% conventional corn silage and 15% conventional corn grain (negative control)
2) 40% Enogen® Feed corn silage and 15% conventional corn grain (corn silage effect)
3) 40% conventional corn silage and 15% Enogen® Feed corn grain (corn grain effect)
4) 40% Enogen® Feed corn silage and 15% Enogen® Feed corn grain (positive control)

The diets for the RC cows are diet 1) (negative control) and 4) (positive control) (e.g. diet sequence as 1)→4)→1)→4) for double crossover).

Samples/Response Variables to Measure:

- Dry Matter Intake: Cows are fed a total mixed ration (TMR) once daily ad libitum, except for the RC cows during sampling period when diets are offered twice daily at 8 am and 8 pm, adjusting the amount offered to have 5-10% of refusals for each cow. Forages are dried to 60° C. for 48 h to adjust the TMR ingredient mixes for variation in dry matter (DM) every week.

Feed ingredient: Individual feed ingredients, TMR, concentrate mix, and orts are sampled once every week and kept frozen for later analysis. Each feed ingredient samples are composited the last two weeks for each period, dried, and ground to pass 1.0 mm sieve in a Wiley mill. Samples are analyzed for gross energy, crude protein (CP), neutral detergent fiber (NDF), undigestible neutral detergent fiber (uNDF) acid detergent fiber (ADF), starch, water soluble carbohydrates, lignin, ether extract, and ash. Orts samples are analyzed for starch, ash, CP, and NDF, and uNDF. In addition, ruminal in vitro NDF digestibility at 30 h, (NDFD30h), ruminal in vitro starch digestibility at 7 h for the composite samples of forages, concentrate mixes (including conventional and Enogen® Feed corn silages and grains) are determined.

Milk Production and Composition: Milk yield is measured daily for each individual cow during the course of the experiment. Cows are milked twice a day AM and PM. Milk samples for milk composition are collected on for two consecutive days (4 milkings) during the last two weeks each period. Milk samples are analyzed for fat, protein, lactose, somatic cell, and MUN concentrations.

Body Weight (BW) and Body condition Score (BCS): Cow's BW and BCS are measured on 2 consecutive days at the beginning of the trial, and during the fourth week of each period.

Enteric methane (CH4) emission: CH4 is measured for each cow during the third week of each period. Methane measurement is conducted multiple times daily with a maximum frequency of every four hour with the GreenFeed system (C-Lock Inc., Rapid City, S.D.). Before the cows are assigned to different dietary treatments, two weeks of adaptation and selection to GreenFeed system are conducted with 20 non-cannulated cows fed the same herd diet. During the two weeks, GreenFeed system are put in front of the cows multiple times to train the cows to get used to the CH4 measurement equipment. At the end of the selection week, the cows that do not adapt to GreenFeed and any additional cows from the protocol are returned to the dairy herd, only 16 cows (in addition to 4 RC cows) are used in assessment of the effect of dietary treatment.

Ruminal fluid sampling: Ruminal fluid is sampled from the 4 RC cows once at 2 and 4 h after feeding each period for analysis of VFA, ammonia and pH profiles.

Rumen pool size and ruminal digesta nutrient: ruminal content is evacuated manually through the ruminal cannula at 12 pm (4 h after feeding) and 7 am (1 h before feeding) on d 21 of (on 3 wk periods) for each of the 4 RC cows each period. Total ruminal content mass and volume are determined and 1 kg subsamples of ruminal digesta is collected for analysis of organic matter (OM), neutral detergent fiber (NDF), undigestible neutral detergent fiber (uNDF) and starch, and the evacuated digesta is placed back in the rumen. Ruminal pool sizes of OM, NDF, uNDF and starch are determined by multiplying the concentration of each component by the ruminal digesta DM.

Omasal digesta sampling: During the last week of each period, digesta flow from the rumen to omasum of RC cows are quantified using the omasal sampling technique developed by Huhtanen et al. (1997. *J Anim Sci.* 75:1380-1392) and modified by Ahvenjarvi et al. (2000, *Br. J. Nutr.* 83: 67-77) and Lopes et al., (2015 *J. Dairy Sci.* 98:574-585). Indigestible NDF, CoEDTA ("Co"), and Lantanum ("La") are used as digesta flow markers for large particle phase, fluid phase, and small particle phase, respectively. Gelatin capsules containing 1 g of La and 0.75 g of Co are dosed through the ruminal cannula at 0600, 1200, 1800, and 0000 h (total of 4 g of La and 3 g of Co per day) for 7 days starting from d 20 of each period, with 3× dosing on d 20. From d 23 to d 25, omasal samples are taken 4 times daily at 2 h intervals to represent the 24 h. Composite omasal samples are separated into 3 omasal phases and analyzed for markers concentration. As a result, omasal apparent digesta flowing out of the rumen are reconstituted. The concentrations of OM, NDF, starch, non-ammonia-N, and microbial N in omasal digesta are determined. The ruminal nutrient digestibility and flow rate are also determined.

In vitro NDF digestibility: Conventional and Enogen® Feed corn silage and corn grain are dried and ground. Triplicates samples are put in ANKOM bags and incubated in buffered ruminal fluid with a water bath at 39° C. for 0, 24, 30, 48 h (4 source of sample×4 time points×triplicates=48 ANKOM bags for samples). Bags are then analyzed for NDF with ANKOM200 Fiber Analyzer (Ankom Technology, Fairport, N.Y.) with α-amylase and sodium sulfide to determine the NDF residue. Then the fiber digestion kinetics of the corn products can be calculated.

Urine spot sample: Spot samples of urine are collected at four time points during the fourth week of each period to cover 24 h. Urine samples are acidified with 0.072 M of sulfuric acid with 4:1 ratio of acid to urine by volume. Urine samples are frozen to −20° C. until analysis. Urine samples are composited into one sample per cow per period and analyzed for total N, urine creatinine, and urine urea. Daily urine volume for each cow is estimated with creatinine in urine as an internal marker. In addition, urine samples composited by diets analyzed for gross energy each period.

Fecal grab sample: Feces samples are taken from the rectum of each cow the same time of urine spot sampling (4 times with 6 h intervals to cover 24 h). Feces samples for each cow are composited by weight and dried, ground, and analyzed for uNDF, NDF, organic matter, total nitrogen, and starch for total tract nutrient digestibility. The daily feces DM output is estimated with uNDF as an internal marker. In addition, feces samples composited by diets are analyzed for gross energy each period. With gross energy from intake and feces and urine, energy balance, including digestible energy and metabolizable energy of the diets, can be determined.

Blood sample: Blood collection is taken from the tail vein up to three times once per period for blood urea nitrogen.

Example 15

Dairy Study with Enogen® Feed Corn as Grain

Multiple on-farm studies indicate a benefit from including Enogen® Feed corn grain in rations fed to lactating dairy cows. In an initial on-farm study, using 6.5 lb/head/day of Enogen® Feed Corn grain to directly replace the same amount of conventional #2 yellow corn grain as part of a balanced ration was shown to protect milk production from a normally expected summer heat-related decrease in output. Each of the conventional corn and Enogen® Feed corn were ground to a particle size of 450 μM, and no other changes were made to the ration composition. While the dairy had routinely experienced a 3-5 lb/head/day drop in milk production in previous years during warmer late spring and summer weather, no decrease in milk production quantity or quality was observed when Enogen® Feed corn grain was included in the rations beginning in late spring (ON Enogen® Feed corn period) versus the previous thirty days (OFF Enogen® Feed corn period) (Table 22). Fecal sample analysis for the ON period showed a 43% reduction in fecal starch vs the OFF period, and an improvement in Apparent Total Tract Starch Digestibility (ATTSD) from 95.42% DM to 98.07% DM.

TABLE 22

Lactation performance, fecal starch and total tract starch digestibility

| Measurement | Conventional grain OFF Period | Enogen ® Feed grain ON period |
|---|---|---|
| Herd size | 1812 | 1818 |
| Average daily milk production (lb/head/day) | 90.75 | 90.69 |
| Fat % | 3.8915 | 3.7856 |
| Protein % | 3.1951 | 3.2165 |
| Fat corrected milk production (lb/head/day) | 96.51 | 94.89 |
| Energy corrected milk production (lb/head/day) | 96.29 | 95.12 |
| Fecal starch % DM | 2.375 | 1.03 |
| ATTSD* % DM | 95.42 | 98.07 |

*Apparent Total Tract Starch Digestibility

In a second dairy location, replacing conventional corn grain (6.5 lb/head/day, 450 μM particle size) with the same amount of Enogen® Feed corn grain in the rations of lactating cows was judged by the attending nutritionist to be beneficial in bringing a difficult epidemic of *Clostridium perfringens* type A under control. This organism, while a normal part of the gut microflora in dairy cows, can under certain conditions including stress, nutritional imbalance, or rumen acidosis, cause serious or fatal disease. The epidemic had been ongoing for 6 months with limited success of the standard antibiotic and antitoxin treatments. Once the herd was switched onto rations containing Enogen® Feed corn grain, treatment success improved and the epidemic was quickly brought to an end. While the mechanism by which this occurred is not fully understood, reduction in rumen acidosis and reduction of excessive starch in the intestines, through increased starch digestibility, might be important factors.

In a third study, ten dairies, representing approximately twelve thousand lactating cows, which all used the same consulting nutritionist and which all received the corn grain included in their herd rations from a single feed mill, participated in a direct replacement study by replacing the conventional corn in their mixed rations with Enogen® Feed corn (6.5 lb/head/day, 450 μM particle size) for 60 to 90 days. No other changes were made to the rations during this period. With this level of inclusion, the previously described summer milk production decline was averted, For the subset of these dairies that gradually increased the inclusion of Enogen® Feed corn grain in the rations to 13.5 lb/head/day, a 2 to 2.5 lb/head day, an increase in milk production was observed with no decline in milk quality parameters.

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

That which is claimed is:

1. A method of increasing the amount of milk produced by a dairy animal, the method comprising feeding to the dairy animal an animal feed comprising transgenic maize plant material, wherein the transgenic maize plant material comprises a polynucleotide encoding a recombinant α-amylase, and wherein the recombinant α-amylase has at least about 80% sequence identity to the amino acid sequence of SEQ ID NO:1.

2. The method of claim 1, wherein the amount of milk produced by the dairy animal is increased by at least about 2% as compared to the amount of milk produced by a control animal that is not provided the animal feed.

3. The method of claim 1, wherein the amount of milk produced by the dairy animal is increased by about 2% to about 50% as compared with the amount of milk produced by a control animal that is not fed the animal feed.

4. The method of claim 1, wherein the dairy animal is a cow.

5. The method of claim 1, wherein the dairy animal is a goat.

6. The method of claim 1, wherein the recombinant α-amylase has at least about 95% sequence identity to the amino acid sequence of SEQ ID NO:1.

7. The method of claim 1, wherein the polynucleotide comprises a nucleotide sequence having at least 80% sequence identity to the nucleotide sequence of SEQ ID NO:2, and/or SEQ ID NO:3.

8. The method of claim 1, wherein the alpha amylase is a thermostable alpha amylase.

9. The method of claim 1, wherein the recombinant α-amylase is α-amylase 797GL3 or D45.

10. The method of claim 1, wherein the maize plant material comprises maize event 3272.

11. The method of claim 1, wherein the recombinant α-amylase is targeted away from its substrate.

12. The method of claim 1, wherein the recombinant α-amylase is targeted to the chloroplast, vacuole, cytoplasm, apoplast or endoplasmic reticulum.

13. The method of claim 1, wherein the recombinant α-amylase is targeted to the endoplasmic reticulum.

14. The method of claim 1, wherein the polynucleotide encoding the recombinant α-amylase is expressed in the kernel.

15. The method of claim 1, wherein the animal feed comprises pellets, grain, silage, dry-rolled kernels, steam flaked kernels, whole kernels, coarsely cracked kernels, high moisture corn, or any combination thereof, comprising the transgenic maize plant material.

16. The method of claim 1, wherein the animal feed comprises at least about 10% by weight on a dry matter basis of the transgenic maize plant material.

17. The method of claim 1, wherein the animal feed is a total mixed ration comprising the transgenic maize plant material.

18. The method of claim 1, wherein the animal feed comprises silage comprising the transgenic maize plant material.

19. The method of claim 1, wherein the animal feed comprises dry-rolled kernels comprising the transgenic maize plant material.

* * * * *

SEQUENCE LISTING

```
<160> NUMBER OF SEQ ID NOS: 5

<210> SEQ ID NO 1
<211> LENGTH: 436
<212> TYPE: PRT
<213> ORGANISM: Artificial
<220> FEATURE:
<223> OTHER INFORMATION: Synthetic

<400> SEQUENCE: 1

Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Ser Gly Gly Tyr Ser Met Gly Tyr Asp
    50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
```

```
        100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Ala Ala Phe
                245                 250                 255

Asp Asn Lys Asn Ile Pro Ala Leu Val Glu Ala Leu Lys Asn Gly Gly
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Ser Ile Val Tyr Tyr Asp Ser Asp Glu Met
            340                 345                 350

Ile Phe Val Arg Asn Gly Tyr Gly Ser Lys Pro Gly Leu Ile Thr Tyr
        355                 360                 365

Ile Asn Leu Gly Ser Ser Lys Val Gly Arg Trp Val Tyr Val Pro Lys
    370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
            420                 425                 430

Cys Gly Val Gly
        435
```

<210> SEQ ID NO 2
<211> LENGTH: 1308
<212> TYPE: DNA
<213> ORGANISM: Artificial
<220> FEATURE:
<223> OTHER INFORMATION: Synthetic

<400> SEQUENCE: 2

```
atggccaagt acctggagct ggaggagggc ggcgtgatca tgcaggcgtt ctactgggac      60

gtcccgagcg gaggcatctg gtgggacacc atccgccaga agatccccga gtggtacgac     120
```

```
gccggcatct ccgcgatctg gataccgcca gcttccaagg gcatgtccgg gggctactcg    180

atgggctacg acccgtacga ctacttcgac ctcggcgagt actaccagaa gggcacggtg    240

gagacgcgct tcgggtccaa gcaggagctc atcaacatga tcaacacggc gcacgcctac    300

ggcatcaagg tcatcgcgga catcgtgatc aaccacaggg ccggcggcga cctggagtgg    360

aacccgttcg tcggcgacta cacctggacg gacttctcca aggtcgcctc cggcaagtac    420

accgccaact acctcgactt ccaccccaac gagctgcacg cgggcgactc cggcacgttc    480

ggcggctacc cggacatctg ccacgacaag tcctgggacc agtactggct ctgggcctcg    540

caggagtcct acgcggccta cctgcgctcc atcggcatcg acgcgtggcg cttcgactac    600

gtcaagggct acggggcctg ggtggtcaag gactggctca actggtgggg cggctgggcg    660

gtgggcgagt actgggacac caacgtcgac gcgctgctca actgggccta ctcctccggc    720

gccaaggtgt tcgacttccc cctgtactac aagatggacg cggccttcga caacaagaac    780

atcccggcgc tcgtcgaggc cctgaagaac ggcggcacgg tggtctcccg cgacccgttc    840

aaggccgtga ccttcgtcgc caaccacgac acggacatca tctggaacaa gtacccggcg    900

tacgccttca tcctcaccta cgagggccag cccacgatct tctaccgcga ctacgaggag    960

tggctgaaca aggacaagct caagaacctg atctggattc acgacaacct cgcgggcggc   1020

tccactagta tcgtgtacta cgactccgac gagatgatct tcgtccgcaa cggctacggc   1080

tccaagcccg gcctgatcac gtacatcaac ctgggctcct ccaaggtggg ccgctgggtg   1140

tacgtcccga agttcgccgg cgcgtgcatc cacgagtaca ccggcaacct cggcggctgg   1200

gtggacaagt acgtgtactc ctccggctgg gtctacctgg aggccccggc ctacgacccc   1260

gccaacggcc agtacggcta ctccgtgtgg tcctactgcg gcgtcggc                1308
```

<210> SEQ ID NO 3
<211> LENGTH: 2223
<212> TYPE: DNA
<213> ORGANISM: Artificial
<220> FEATURE:
<223> OTHER INFORMATION: Synthetic

<400> SEQUENCE: 3

```
atggccaagt acctggagct ggaggagggc ggcgtgatca tgcaggcgtt ctactgggac     60

gtcccgagcg gaggcatctg gtgggacacc atccgccaga agatccccga gtggtacgac    120

gccggcatct ccgcgatctg gataccgcca gcttccaagg gcatgtccgg gggctactcg    180

atgggctacg acccgtacga ctacttcgac ctcggcgagt actaccagaa gggcacggtg    240

gagacgcgct tcgggtccaa gcaggagctc atcaacatga tcaacacggc gcacgcctac    300

ggcatcaagg tcatcgcgga catcgtgatc aaccacaggg ccggcggcga cctggagtgg    360

aacccgttcg tcggcgacta cacctggacg gacttctcca aggtcgcctc cggcaagtac    420

accgccaact acctcgactt ccaccccaac gagctgcacg cgggcgactc cggcacgttc    480

ggcggctacc cggacatctg ccacgacaag tcctgggacc agtactggct ctgggcctcg    540

caggagtcct acgcggccta cctgcgctcc atcggcatcg acgcgtggcg cttcgactac    600

gtcaagggct acggggcctg ggtggtcaag gactggctca actggtgggg cggctgggcg    660

gtgggcgagt actgggacac caacgtcgac gcgctgctca actgggccta ctcctccggc    720

gccaaggtgt tcgacttccc cctgtactac aagatggacg cggccttcga caacaagaac    780

atcccggcgc tcgtcgaggc cctgaagaac ggcggcacgg tggtctcccg cgacccgttc    840

aaggccgtga ccttcgtcgc caaccacgac acggacatca tctggaacaa gtacccggcg    900
```

```
tacgccttca tcctcaccta cgagggccag cccacgatct tctaccgcga ctacgaggag    960

tggctgaaca aggacaagct caagaacctg atctggattc acgacaacct cgcgggcggc   1020

tccactagta tcgtgtacta cgactccgac gagatgatct tcgtccgcaa cggctacggc   1080

tccaagcccg gcctgatcac gtacatcaac ctgggctcct ccaaggtggg ccgctgggtg   1140

tacgtcccga agttcgccgg cgcgtgcatc cacgagtaca ccggcaacct cggcggctgg   1200

gtggacaagt acgtgtactc ctccggctgg gtctacctgg aggccccggc ctacgacccc   1260

gccaacggcc agtacggcta ctccgtgtgg tcctactgcg gcgtcggcac atcgattgct   1320

ggcatcctcg aggccgacag ggtcctcacc gtcagcccct actacgccga ggagctcatc   1380

tccggcatcg ccaggggctg cgagctcgac aacatcatgc gcctcaccgg catcaccggc   1440

atcgtcaacg gcatggacgt cagcgagtgg gaccccagca gggacaagta catcgccgtg   1500

aagtacgacg tgtcgacggc cgtggaggcc aaggcgctga acaaggaggc gctgcaggcg   1560

gaggtcgggc tcccggtgga ccggaacatc ccgctggtgg cgttcatcgg caggctggaa   1620

gagcagaagg gccccgacgt catggcggcc gccatcccgc agctcatgga gatggtggag   1680

gacgtgcaga tcgttctgct gggcacgggc aagaagaagt tcgagcgcat gctcatgagc   1740

gccgaggaga agttcccagg caaggtgcgc gccgtggtca agttcaacgc ggcgctggcg   1800

caccacatca tggccggcgc cgacgtgctc gccgtcacca gccgcttcga gccctgcggc   1860

ctcatccagc tgcaggggat gcgatacgga acgccctgcg cctgcgcgtc caccggtgga   1920

ctcgtcgaca ccatcatcga aggcaagacc gggttccaca tgggccgcct cagcgtcgac   1980

tgcaacgtcg tggagccggc ggacgtcaag aaggtggcca ccaccttgca gcgcgccatc   2040

aaggtggtcg gcacgccggc gtacgaggag atggtgagga actgcatgat ccaggatctc   2100

tcctggaagg gccctgccaa gaactgggag aacgtgctgc tcagcctcgg ggtcgccggc   2160

ggcgagccag gggttgaagg cgaggagatc gcgccgctcg ccaaggagaa cgtggccgcg   2220

ccc                                                                 2223
```

<210> SEQ ID NO 4
<211> LENGTH: 3285
<212> TYPE: DNA
<213> ORGANISM: Aspergillus shirousami

<400> SEQUENCE: 4

```
gccaccccgg ccgactggcg ctcccagtcc atctacttcc tcctcaccga ccgcttcgcc     60

cgcaccgacg gctccaccac cgccacctgc aacaccgccg accagaagta ctgcggcggc    120

acctggcagg gcatcatcga caagctcgac tacatccagg gcatgggctt caccgccatc    180

tggatcaccc cggtgaccgc ccagctcccg cagaccaccg cctacggcga cgcctaccac    240

ggctactggc agcaggacat ctactccctc aacgagaact acggcaccgc cgacgacctc    300

aaggccctct cctccgccct ccacgagcgc ggcatgtacc tcatggtgga cgtggtggcc    360

aaccacatgg gctacgacgg cgccggctcc tccgtggact actccgtgtt caagccgttc    420

tcctcccagg actacttcca cccgttctgc ttcatccaga actacgagga ccagacccag    480

gtggaggact gctggctcgg cgacaacacc gtgtccctcc cggacctcga caccaccaag    540

gacgtggtga agaacgagtg gtacgactgg gtgggctccc tcgtgtccaa ctactccatc    600

gacggcctcc gcatcgacac cgtgaagcac gtgcagaagg acttctggcc cgggctacaac    660

aaggccgccg gcgtgtactg catcggcgag gtgctcgacg tggacccggc ctacacctgc    720
```

```
ccgtaccaga acgtgatgga cggcgtgctc aactacccga tctactaccc gctcctcaac    780
gccttcaagt ccacctccgg ctcgatggac gacctctaca acatgatcaa caccgtgaag    840
tccgactgcc cggactccac cctcctcggc accttcgtgg agaaccacga caacccgcgc    900
ttcgcctcct acaccaacga catcgccctc gccaagaacg tggccgcctt catcatcctc    960
aacgacggca tcccgatcat ctacgccggc caggagcagc actacgccgg cggcaacgac   1020
ccggccaacc gcgaggccac ctggctctcc ggctacccga ccgactccga gctgtacaag   1080
ctcatcgcct ccgccaacgc catccgcaac tacgccatct ccaaggacac cggcttcgtg   1140
acctacaaga actggccgat ctacaaggac gacaccacca tcgccatgcg caagggcacc   1200
gacggctccc agatcgtgac catcctctcc aacaagggcg cctccggcga ctcctacacc   1260
ctctccctct ccggcgccgg ctacaccgcc ggccagcagc tcaccgaggt gatcggctgc   1320
accaccgtga ccgtgggctc cgacggcaac gtgccggtgc cgatggccgg cggcctcccg   1380
cgcgtgctct acccgaccga gaagctcgcc ggctccaaga tatgctcctc ctccaagccg   1440
gccaccctcg actcctggct ctccaacgag gccaccgtgg cccgcaccgc catcctcaac   1500
aacatcggcg ccgacggcgc ctgggtgtcc ggcgccgact ccggcatcgt ggtggcctcc   1560
ccgtccaccg acaacccgga ctacttctac acctggaccc gcgactccgg catcgtgctc   1620
aagaccctcg tggacctctt ccgcaacggc gacaccgacc tcctctccac catcgagcac   1680
tacatctcct cccaggccat catccagggc gtgtccaacc cgtccggcga cctctcctcc   1740
ggcggcctcg gcgagccgaa gttcaacgtg gacgagaccg cctacgccgg ctcctggggc   1800
cgcccgcagc gcgacggccc ggccctccgc gccaccgcca tgatcggctt cggccagtgg   1860
ctcctcgaca acggctacac ctccgccgcc accgagatcg tgtggccgct cgtgcgcaac   1920
gacctctcct acgtggccca gtactggaac cagaccggct acgacctctg ggaggaggtg   1980
aacggctcct ccttcttcac catcgccgtg cagcaccgcg ccctcgtgga gggctccgcc   2040
ttcgccaccg ccgtgggctc ctcctgctcc tggtgcgact cccaggcccc gcagatcctc   2100
tgctacctcc agtccttctg gaccggctcc tacatcctcg ccaacttcga ctcctcccgc   2160
tccggcaagg acaccaacac cctcctcggc tccatccaca ccttcgaccc ggaggccggc   2220
tgcgacgact ccaccttcca gccgtgctcc ccgcgcgccc tcgccaacca caaggaggtg   2280
gtggactcct tccgctccat ctacaccctc aacgacggcc tctccgactc cgaggccgtg   2340
gccgtgggcc gctacccgga ggactcctac tacaacggca acccgtggtt cctctgcacc   2400
ctcgccgccg ccgagcagct ctacgacgcc ctctaccagt gggacaagca gggctccctg   2460
gagatcaccg acgtgtccct cgacttcttc aaggccctct actccggcgc cgccaccggc   2520
acctactcct cctcctcctc cacctactcc tccatcgtgt ccgccgtgaa gaccttcgcc   2580
gacggcttcg tgtccatcgt ggagacccac gccgcctcca acggctccct ctccgagcag   2640
ttcgacaagt ccgacggcga cgagctgtcc gcccgcgacc tcacctggtc ctacgccgcc   2700
ctcctcaccg ccaacaaccg ccgcaactcc gtggtgccgc cgtcctgggg cgagacctcc   2760
gcctcctccg tgccgggcac ctgcgccgcc acctccgcct ccggcaccta ctcctccgtg   2820
accgtgacct cctggccgtc catcgtggcc accggcggca ccaccaccac cgccaccacc   2880
accggctccg gcggcgtgac ctccacctcc aagaccacca ccaccgcctc caagacctcc   2940
accaccacct cctccacctc ctgcaccacc ccgaccgccg tggccgtgac cttcgacctc   3000
accgccacca ccacctacgg cgagaacatc tacctcgtgg gctccatctc ccagctcggc   3060
gactgggaga cctccgacgg catcgccctc tccgccgaca agtacacctc ctccaacccg   3120
```

```
ccgtggtacg tgaccgtgac cctcccggcc ggcgagtcct tcgagtacaa gttcatccgc   3180

gtggagtccg acgactccgt ggagtgggag tccgacccga accgcgagta caccgtgccg   3240

caggcctgcg gcgagtccac cgccaccgtg accgacacct ggcgc                   3285


<210> SEQ ID NO 5
<211> LENGTH: 1320
<212> TYPE: DNA
<213> ORGANISM: Artificial
<220> FEATURE:
<223> OTHER INFORMATION: Synthetic

<400> SEQUENCE: 5

atggcgaagc acttggctgc catgtgctgg tgcagcctcc tagtgcttgt actgctctgc     60

ttgggctccc agctggccca atcccaggtc ctcttccagg ggttcaactg ggagtcgtgg    120

aagaagcaag gtgggtggta caactacctc ctggggcggg tggacgacat cgccgcgacg    180

ggggccacgc acgtctggct cccgcagccg tcgcactcgg tggcgccgca ggggtacatg    240

cccggccggc tctacgacct ggacgcgtcc aagtacggca cccacgcgga gctcaagtcg    300

ctcaccgcgg cgttccacgc caagggcgtc cagtgcgtcg ccgacgtcgt gatcaaccac    360

cgctgcgccg actacaagga cggccgcggc atctactgcg tcttcgaggg cggcacgccc    420

gacagccgcc tcgactgggg ccccgacatg atctgcagcg acgacacgca gtactccaac    480

gggcgcgggc accgcgacac gggggccgac ttcgccgccg cgcccgacat cgaccacctc    540

aacccgcgcg tgcagcagga gctctcggac tggctcaact ggctcaagtc cgacctcggc    600

ttcgacggct ggcgcctcga cttcgccaag ggctactccg ccgccgtcgc caaggtgtac    660

gtcgacagca ccgcccccac cttcgtcgtc gccgagatat ggagctccct ccactacgac    720

ggcaacggcg agccgtccag caaccaggac gccgacaggc aggagctggt caactgggcg    780

caggcggtgg gcggccccgc cgcggcgttc gacttcacca ccaagggcgt gctgcaggcg    840

gccgtccagg gcgagctgtg gcgcatgaag gacggcaacg gcaaggcgcc cgggatgatc    900

ggctggctgc cggagaaggc cgtcacgttc gtcgacaacc acgacaccgg ctccacgcag    960

aactcgtggc cattcccctc cgacaaggtc atgcagggct acgcctatat cctcacgcac   1020

ccaggaactc catgcatctt ctacgaccac gttttcgact ggaacctgaa gcaggagatc   1080

agcgcgctgt ctgcggtgag gtcaagaaac gggatccacc cggggagcga gctgaacatc   1140

ctcgccgccg acggggatct ctacgtcgcc aagattgacg acaaggtcat cgtgaagatc   1200

gggtcacggt acgacgtcgg gaacctgatc ccctcagact tccacgccgt tgcccctggc   1260

aacaactact gcgtttggga gaagcacggt ctgagagttc cagcggggcg gcaccactag   1320
```